US012249429B2

(12) United States Patent
Futamura

(10) Patent No.: US 12,249,429 B2
(45) Date of Patent: Mar. 11, 2025

(54) COMPUTER-ASSISTED MODELING FOR TREATMENT DESIGN

(71) Applicant: Hinge Therapeutics, Inc., Sunnyvale, CA (US)

(72) Inventor: Akiko Futamura, Sunnyvale, CA (US)

(73) Assignee: Hinge Therapeutics, Inc., Sunnyvale, CA (US)

( * ) Notice: Subject to any disclaimer, the term of this patent is extended or adjusted under 35 U.S.C. 154(b) by 1615 days.

(21) Appl. No.: 15/978,468

(22) Filed: May 14, 2018

(65) Prior Publication Data

US 2018/0261331 A1 Sep. 13, 2018

Related U.S. Application Data

(63) Continuation of application No. 14/543,418, filed on Nov. 17, 2014, now abandoned.

(60) Provisional application No. 61/905,073, filed on Nov. 15, 2013.

(51) Int. Cl.
| | |
|---|---|
| *G16H 50/50* | (2018.01) |
| *G06F 16/21* | (2019.01) |
| *G16B 15/00* | (2019.01) |
| *G16B 15/30* | (2019.01) |
| *G16C 20/50* | (2019.01) |
| *G16H 50/20* | (2018.01) |

(52) U.S. Cl.
CPC .............. *G16H 50/50* (2018.01); *G06F 16/21* (2019.01); *G16B 15/00* (2019.02); *G16B 15/30* (2019.02); *G16C 20/50* (2019.02); *G16H 50/20* (2018.01)

(58) Field of Classification Search
CPC ................................ G16H 50/50; G16H 50/20
See application file for complete search history.

(56) References Cited

U.S. PATENT DOCUMENTS

| | | | |
|---|---|---|---|
| 7,826,979 B2 | 11/2010 | Bemis et al. | |
| 2006/0141480 A1 | 6/2006 | Ramnarayan et al. | |
| 2013/0297643 A1 | 11/2013 | Dettinger et al. | |
| 2015/0133307 A1* | 5/2015 | Zhang .................... | G16B 35/20 506/1 |
| 2015/0142408 A1 | 5/2015 | Futamura | |

FOREIGN PATENT DOCUMENTS

| | | |
|---|---|---|
| JP | 2001289847 A | 10/2001 |
| JP | 2004152029 A | 5/2004 |
| JP | 2007502106 A | 2/2007 |
| JP | 2012515330 A | 7/2012 |

OTHER PUBLICATIONS

Futamura, The Role of Reactive Center Loop in Serpin, 2002, University of Illinois, p. 1-144 (Year: 2002).*
Spiess, Treating Heparin Resistance with Antithrombin or Fresh Frozen Plasma, 2008, Ann Thorac. Surg., 85, p. 2153-2160 (Year: 2008).*
Vorburger et al., Adenoviral Gene Therapy, 2002, The Oncologist, 7, p. 46-59 (Year: 2002).*
Skinner et al., Implications for Function and Therapy of a 2.9 A Structure of Binary-complexed Antithrombin, 1998, J. Mol. Biol., 283, p. 9-14 (Year: 1998).*
Kent, Total chemical synthesis of proteins, Chem. Soc. Rev., 2009, 38, p. 338-351 (Year: 2009).*
Hird, Automated synthesis: new tools for the organic chemist, 1999, DDT, 4(6), p. 265-274 (Year: 1999).*
Lionta et al., Structure-Based Virtual Screening for Drug Discovery: Principles, Applications and Recent Advances, 2014, 14, p. 1923-1938 (Year: 2014).*
Notification of Reasons for Refusal for Japanese Application No. 2016-554536; Date of Mailing: Dec. 14, 2018; 8 pages.
European Search Report mailed Nov. 27, 2017 for European Patent Application No. 14861413.4, 16 pages.
Flores, Samuel C., et al., "Hinge Atlas: relating protein sequence to sites of structural flexibility", BMC Bioinformatics 2007, 8:167, http://www.biomedcentral.com/1471-2105/167, May 22, 2007, pp. 1-20.
Final Office Action Mailed Dec. 2, 2016 of U.S. Appl. No. 14/543,418 by A. Futamura, filed Nov. 17, 2014.
Final Office Action Mailed Oct. 20, 2017 of U.S. Appl. No. 14/543,418 by A. Futamura, filed Nov. 17, 2014.
Non-Final Office Action Mailed May 10, 2016 of U.S. Appl. No. 14/543,418 by A. Futamura, filed Nov. 17, 2014.
Restriction Requirement Mailed Mar. 23, 2016 of U.S. Appl. No. 14/543,418 by A. Futamura, filed Nov. 17, 2014.

(Continued)

*Primary Examiner* — Kaitlyn L Minchella
(74) *Attorney, Agent, or Firm* — Procopio, Cory, Hargreaves & Savitch LLP

(57) ABSTRACT

Some embodiments include a computer-assisted method of biomedical treatment design. For example, a computer system can select a compound model associated with a candidate compound that is structured to bind to a biological target to modulate the biological target into achieving a therapeutic effect. The computer system can then identify a structural feature in the compound model as a hinge region that connects domains in the candidate compound. The computer system then determines a mutation process to introduce a mutation at the hinge region such that the mutation activates the candidate compound. The computer system then generates an updated compound model based on the mutation added to the candidate compound to present in a treatment design interface.

23 Claims, 16 Drawing Sheets

(56) References Cited

OTHER PUBLICATIONS

Written Opinion and Search Report Mailed Apr. 9, 2015 of International Application No. PCT/US2014/065955 by A. Futamura, filed Nov. 17, 2014.

Futamura, Akiko et al., "Serine 380 (P14)—Glutamate Mutation Activates Antithrombin as an Inhibitor of Factor Xa*", J. Bio. Chem., vol. 275, No. 6, 2000, 4092-4098.

Hopkins, Paul C. et al., "Effects of Mutations in the Hinge Region of Serpins", Biochemistry, 32, 1993, 7650-7657.

* cited by examiner

```
                                                            600
```

```
┌─────────────────────────────────────────────────────────────────┐
│ Select a compound model associated with a candidate compound    │
│ that is structured to bind to a biological target to modulate   │
│ the biological target into achieving a therapeutic effect       │
│                            602                                  │
└─────────────────────────────────────────────────────────────────┘
                                │
                                ▼
┌─────────────────────────────────────────────────────────────────┐
│ Identify a structural feature in the compound model as a hinge  │
│ region that connects stable domains in the candidate compound   │
│                            604                                  │
└─────────────────────────────────────────────────────────────────┘
                                │
                                ▼
┌─────────────────────────────────────────────────────────────────┐
│           Compute a mutation process for the hinge region       │
│                            606                                  │
└─────────────────────────────────────────────────────────────────┘
                                │
                                ▼
┌─────────────────────────────────────────────────────────────────┐
│ Generate an updated compound model based on the mutation added  │
│ to the candidate compound to present in a treatment design      │
│ interface                                                       │
│                            608                                  │
└─────────────────────────────────────────────────────────────────┘
                                │
                                ▼
┌─────────────────────────────────────────────────────────────────┐
│ Determine a free peptide model that is capable of binding to    │
│ the hinge region to deactivate the candidate compound           │
│                            610                                  │
└─────────────────────────────────────────────────────────────────┘
                                │
                                ▼
┌─────────────────────────────────────────────────────────────────┐
│     Present the free peptide model via the treatment design     │
│                          interface                              │
│                            612                                  │
└─────────────────────────────────────────────────────────────────┘
                                │
                                ▼
┌─────────────────────────────────────────────────────────────────┐
│  Generate and present a treatment plan via the treatment design │
│                          interface                              │
│                            614                                  │
└─────────────────────────────────────────────────────────────────┘
```

┌─────────────────────────────────────────────────────────────────────┐
│              Generate a compound model for a functional compound    │
│                                    702                              │
└─────────────────────────────────────────────────────────────────────┘
                                   │
                                   ▼
┌─────────────────────────────────────────────────────────────────────┐
│ Identify a structural feature in the compound model of the functional compound as a │
│   hinge region that connects stable domains in the functional compound              │
│                                    704                              │
└─────────────────────────────────────────────────────────────────────┘
                                   │
                                   ▼
┌─────────────────────────────────────────────────────────────────────┐
│ Model a mutation at the hinge region associated with the compound model such that   │
│  the mutation activates the functional compound when introduced to the functional   │
│                                 compound                            │
│                                    706                              │
└─────────────────────────────────────────────────────────────────────┘
                                   │
                                   ▼
┌─────────────────────────────────────────────────────────────────────┐
│  Receive test data associated with the hinge region of the functional compound via a │
│                        treatment design interface                   │
│                                    708                              │
└─────────────────────────────────────────────────────────────────────┘
                                   │
                                   ▼
┌─────────────────────────────────────────────────────────────────────┐
│  Determine an activation behavior associated with the hinge region based on the test │
│                                   data                              │
│                                    710                              │
└─────────────────────────────────────────────────────────────────────┘
                                   │
                                   ▼
┌─────────────────────────────────────────────────────────────────────┐
│ Associate the structural feature with the activation behavior and the compound model │
│                        in a hinge region database                   │
│                                    712                              │
└─────────────────────────────────────────────────────────────────────┘
                                   │
                                   ▼
┌─────────────────────────────────────────────────────────────────────┐
│ Index the hinge region database to configure one or more biomedical treatment plans │
│  including a treatment plan to modify a specific hinge region of a candidate compound│
│     to activate the candidate compound based on the hinge region database           │
│                                    714                              │
└─────────────────────────────────────────────────────────────────────┘
```

*FIG. 7*

| Example Applications | Functional Compound Examples | Potential Results |
|---|---|---|
| Reprograming | • Transcription factors<br>• kinases | Fast DNA binding -> better regulation, better yield (more complete reprogramming) |
| Differentiation | • Phosphorylation of transcription factors, kinases<br>Eg. MAP kinases | Faster DNA binding Better regulation "planned" and "predictable" activation |
| Therapy | • Structural protein Integrin, dystrophin<br>• Anti-inflammatory proteins | Fast assembly -> more therapeutic efficacy -> requires fewer cells |

*FIG. 9*

COMPUTER-ASSISTED MODELING FOR TREATMENT DESIGN

CROSS-REFERENCE TO RELATED APPLICATIONS

This application is a continuation of U.S. patent application Ser. No. 14/543,418, titled "COMPUTER-ASSISTED MODELING FOR TREATMENT DESIGN" and filed on Nov. 17, 2014, which claims the benefit of U.S. Provisional Patent Application No. 61/905,073, titled "HINGE REGION SELECTION FOR BIOMEDICAL THERAPY" and filed on Nov. 15, 2013, each of which is incorporated by reference herein in its entirety.

TECHNICAL FIELD

This disclosure relates to computer-assisted treatment design.

BACKGROUND

Present day biomedical therapy and treatment may include drug treatment, cell therapy (e.g., stem cell-specific therapeutics), gene therapy (e.g., gene activation), induced pluripotent stem (iPS) cell derivative (reprogramming), antibody therapy, other types of in-vivo therapy involving biological effectors acting within a living body or cell culture, other types of in-vitro therapy, or any combination thereof. These biomedical therapy may involve a functional compound, such as a drug, an enzyme compound, a protein/DNA/RNA binding compound (e.g., for gene activation), or an antibody (such as immunoglobulin with an antigen binding region and/or effector function region) that binds and modulates a biological target (e.g., organic material inside a living body or a cell culture).

In typical biomedical treatment design (e.g., computer-assisted drug design), a computer system can model a functional compound having a functional region (e.g., an activity domain) capable of interacting with and modulating a specific biological target (e.g., a specific protein or gene). Identification of the proper functional region that can bind with the specific biological target can be based on a structured-based design (e.g., relying on the knowledge of the three-dimensional structure of the biological target) or ligand-based design (e.g., relying on the knowledge of other molecules that can bind to the biological target).

In order to design a functional compound suitable for a biomedical therapy, a rational drug discovery methodology can be deployed. In contrast to traditional methods of drug discovery, which rely on trial-and-error testing of chemical substances on culture cells or animals, and matching the apparent effects to treatments, rational drug design begins with a hypothesis that modulation of a specific biological target (e.g., a drug target or a mutation target) may have therapeutic value. For example, a biological target can be a key molecule involved in a particular metabolic or signaling pathway that is specific to a disease condition or pathology or to the infectivity or survival of a microbial pathogen. A biological target can be selected by a computer system if the modulation of the biological target is confirmed to have therapeutic effects and if the activity of the biological target can be modulated by a functional compound (e.g., the biological target is capable of binding to the functional compound, such as a small molecule or a protein). A small molecule in this context is a low molecular weight organic compound that helps to regulate a biological process.

In computer-aided treatment design (e.g., computer-aided drug design), computational chemistry can be used to discover, enhance, or study functional compounds and related biological active molecules. A fundamental goal of computer aided treatment design is to predict whether a given molecule/compound will bind to a target, and if so, how strongly. Molecular mechanics or molecular dynamics are often used to compute the conformation of a small molecule and to model conformational changes in the biological target that may occur when the small molecule binds to it. Several methods for predicting drug metabolism have been proposed. However, due to the complexity of the treatment design process, and the large amount of chemical space that any potential new drug can have, it is difficult to design an effective drug using a computer-assisted ab initio treatment design process.

BRIEF DESCRIPTION OF THE DRAWINGS

FIG. 6 is a flow chart illustrating a computer-assisted method of designing a biomedical treatment, in accordance with various embodiments.

FIG. 7 is a flow chart illustrating a computer-assisted method of building a compound optimization database, in accordance with various embodiments.

FIG. 9 is a table illustrating different applications of activating functional compounds, in accordance with various embodiments.

DETAILED DESCRIPTION

Figure 1:
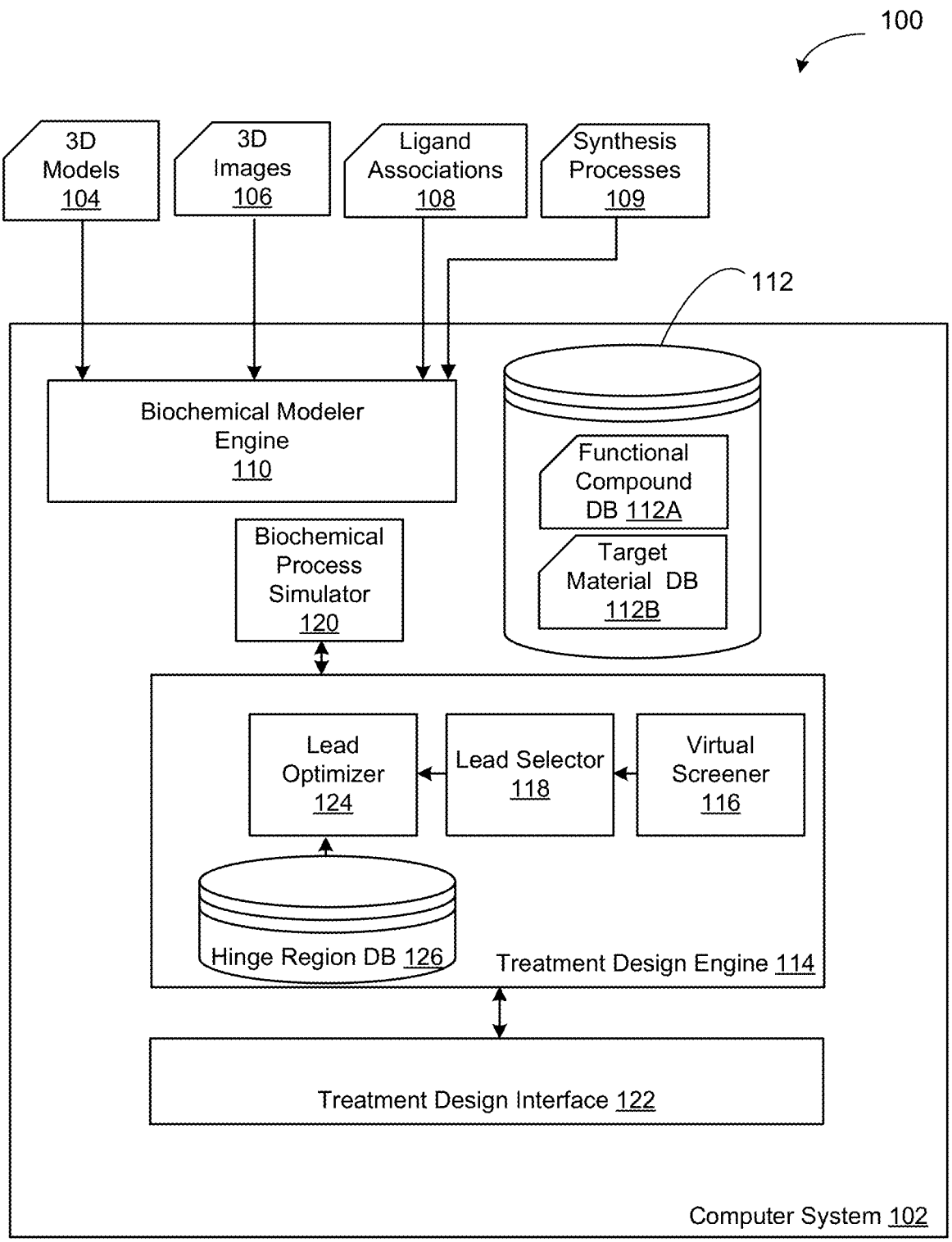
FIG. 1 is a block diagram illustrating a computer-implemented treatment design system, in accordance with various embodiments.

A rational treatment design process can identify a functional compound (e.g., a small molecule or protein) designed specifically for a biomedical treatment. The functional compound is "functional" in the sense that it can modulate a biological target, e.g., a biological target. In some embodiments, the functional compound is synthesized, such as a potential drug; and in other embodiments, the functional compound is already present in a living body of an organism. To optimize for the efficacy of the potential drug for the particular biomedical treatment, the potential drug may be modified during treatment or before treatment. To utilize a functional compound already inside a living body, the treatment plan may involve introducing a biochemical agent to "activate" the functional compound.

For example, the functional compound may not interact with its biological targets frequently enough to sufficiently modulate enough of the biological targets. That is, while in an inactive state, a functional region of the functional compound may not sufficiently interact with the biological target to cause a therapeutic effect. Conventionally, an activating agent may be used in conjunction with the functional compound to activate the functional compound. Under the conventional method, a biomedical treatment may require an activation agent to bring the drug into an active state. For example, a biomedical treatment can include administering both the functional compound and the activation agent to a living body to "activate" the potential drug during treatment. In several embodiments, a computing system can compute a mutation that can be introduced to the functional compound before treatment or during treatment to activate the functional region without the activation agent.

Functional compounds (e.g., used as potential drugs or naturally in a living body) can have an activated state and an inactivated state. A functional compound can include a functional region. When activated, the functional region can interact with a biological target. In some embodiments, the functional compound itself is an organic material. For example, the biological target may be specific types of cells, specific regions of DNA, specific proteins, or any combination thereof.

Several embodiments include computer-assisted methods of identifying how to modify a functional compound to ensure that the functional compound maintains an active state, even without the help of an activation agent. For example, a computer system can identify a hinge region within a functional compound. This can be achieved by performing a structural scan of the functional compound. This can be achieved by accessing a three-dimensional model or three-dimensional image of the functional compound stored in the computer system (e.g., as part of the initial treatment design process). In response to identifying the hinge region, the computer system can select a suggested mutation at the hinge region to "open up" the functional region for binding or interaction with the target organic material (herein referred to as a "biological target").

A hinge region may exist within the functional compound. The hinge region is an interconnecting region of the functional compound connecting domains (e.g., stable domains) of the functional compound. The hinge region can connect at least a domain with the functional region of the functional compound. In some embodiments, the functional region may be part of one of the domains. Domains may be regions of a protein chain that are folded onto itself. For example, a domain may be a region that contains one or more intra-chain bonds (e.g., disulfide bond).

In some cases, a hinge region may provide flexibility between at least two ends (e.g., as defined by the domains) of the functional compound. A nonfunctional domain (e.g., an inert domain) being close to the functional region may sometimes cause the functional region to be inactive. Conventionally, the activation agent is introduced in an environment of a functional compound such that the activation agent can bind to the functional compound to activate the functional region. In several embodiments the computer system can identify a site in the hinge region to introduce a mutation. In many cases, the mutation at the hinge region can distance the non-functional domain from the functional region such that the functional region remains active or a higher degree of "activeness." This may be achieved when the mutation opens up domains connected to the hinge region. For example, the mutation can repel the domains from the functional region or vice versa. The computer system can design a hinge region to increase the efficacy of the functional compounds multiple folds. For example, in stem cell therapy, size of an amino acid structure in a hinge region of a functional compound may be adjusted (e.g., increased) to increase the efficacy of the functional compound by 1000 folds.

Accordingly, a computer implemented process of designing potential compounds for biomedical treatment can depend on a hinge region database. The hinge region database can characterize potential hinge regions between domains of a functional compound. To design a treatment plan, a computer system can first identify one or more functional compounds that are effective in binding to a biological target. The computer system can then identify one or more hinge regions of the functional compounds that may be modified. For example, the computing system can identify and suggest a mutation to introduce into at least one of the hinge regions in the functional compounds to open up domains of the functional compounds and subsequently "activate" the functional compounds.

FIG. 1 is a block diagram illustrating a computer-implemented treatment design system 100, in accordance with various embodiments. The computer-implemented treatment design system 100 can be implemented by a computer system 102, such as the computer system 800 of FIG. 8. The computer system 102 can be implemented by one or more computing devices. The computer-implemented treatment design system 100 can implement a computer-assisted ab initio drug design process. The computer system 102 can receive data characterizing functional compounds (e.g., small molecules and proteins) and biological targets (e.g., biological molecules, living cells, microbes, DNA, other organic material, or any combination thereof) from one or more external computers. For example, the external computers can provide three-dimensional structural models 104 of the functional compounds, three-dimensional images 106 of the functional compounds (e.g., using a form of scanning electron microscopy), ligand associations 108 referencing ligands that can bind to the biological targets and/or the functional compounds, synthesis processes 109 for biochemically synthesizing the functional compounds (e.g., for the functional compounds that can be synthesized), or any combination thereof.

The computer system 102 can include a biochemical modeler engine 110. The biochemical modeler engine 110 can configure a processor (not shown) of the computer system 102 to process and aggregate the information (e.g., the three-dimensional structural models 104, these three-dimensional images 106, the ligand associations 108, and the synthesis processes 109) associated with the functional compounds and the biological targets into a model store 112. The biochemical modeler engine 110 can format the information associated with the functional compounds from various sources into a database of models, each model referencing the information associated with a functional compound (e.g., the information is organized according to structural portions of each functional compound). Likewise, the biochemical modeler engine 110 can format the information associated with the biological targets from various sources into a database of models, each model referencing the information associated with a biological target (e.g., the information is organized according to structural portions of each biological target). For example, the model store 112 can have a functional compound database 112A storing one or more functional compound models and a target material database 112B storing one or more biological target models.

The computer system 102 can include a treatment design engine 114. The treatment design engine 114 can configure the processor to generate a structural model of a functional compound that will bind to a biological target and that is optimized to modulate the biological target to achieve a therapeutic effect.

For example, the treatment design engine 114 can include a virtual screener engine 116. The virtual screener engine 116 can perform a virtual screening of candidate compounds by referencing the model store 112. Virtual screening is a computational technique for drug discovery to search a database of potential functional compounds to identify structures which are most likely to bind to a biological target (e.g., one of the structures described in the target material database 112B). In some embodiments, virtual screening includes an automatic evaluation of compound structures by comparing the structures of a candidate compound against a receptor area of the biological target. In some embodiments, virtual screening includes identifying ligands that bind to a receptor area of the biological target, and determining the similarity between the ligands and a candidate compound. In some embodiments, the virtual screener engine 116 can output a list of candidate compounds from the screening process.

After the virtual screening, the selected candidate compounds can be provided to a lead selector engine 118. The lead selector engine 118 can select a subset of the candidate compounds as one or more lead candidate compounds to be used in a biomedical treatment. The lead selector engine 118 can confirm and evaluate the candidate compounds in accordance with a number of evaluation processes, including for example, biochemical testing, toxicity verification, dose response, orthogonal testing, secondary structural screening, synthesis feasibility evaluation, biophysical testing (e.g., nuclear magnetic resonance, isothermal titration calorimetry, dynamic light scattering, surface plasmon resonance, dual polarization interferometry, microscale thermophoresis, etc.), or any combination thereof. In some cases, the evaluation processes can be verified logically as computational processes (e.g., in reference to a model of the biological target and a model of a lead candidate compound in the model store 112) in the computer system 102. For example, a biochemical process simulator 120 can logically evaluate the synthesis feasibility, biophysical characteristics, and/or dose response characteristics of the candidate compounds. In some embodiments, the virtual screener engine 116 can identify analogs of the confirmed lead candidate compounds to expand the list of potential lead candidate compounds.

In some cases, the evaluation processes can include external testing (e.g., assays) performed by human actors who report back the results of the evaluation processes via a treatment design interface 122. The treatment design interface 122 is a graphical user interface implemented on the computer system 102. The treatment design interface 122 enables the lead selector engine 118 to present the candidate compounds and the necessary evaluation processes to a user. The treatment design interface 122 also enables the user to input the results of the evaluation processes back to the treatment design engine 114.

The treatment design engine 114 can include a lead optimizer engine 124. The lead optimizer engine 124 can compute modifications to a lead candidate compound from the lead selector engine 118 to optimize for pharmaceutical properties or therapeutic values while maintaining affinity of the lead candidate compound to the biological target. In several embodiments, a hinge region database 126 is utilized in the lead optimizer engine 124 to design mutations to the lead candidate compound to optimize the therapeutic efficacy of the lead candidate compound, for example, by introducing a mutation that activates the lead candidate compound without an activation agent (e.g., a co-factor to the treatment).

In various embodiments, the treatment design interface 122 can present a final model of the lead candidate compound together with any suggested mutation to optimize its therapeutic efficacy. In some embodiments, the treatment design interface 122 can present a synthesis process associated with the lead candidate compound according to the functional compound database 112A (e.g., according to one of the synthesis processes 109). This enables a user (e.g., a pharmaceutical technician) to create the lead candidate compound. In some embodiments, the treatment design interface 122 is coupled to a synthesizer machine (not shown). In those embodiments, the treatment design interface 122 can provide the model of the lead candidate compound to the synthesizer machine to facilitate synthesis of the lead synthesizer compound automatically or semi automatically.

Figure 2:
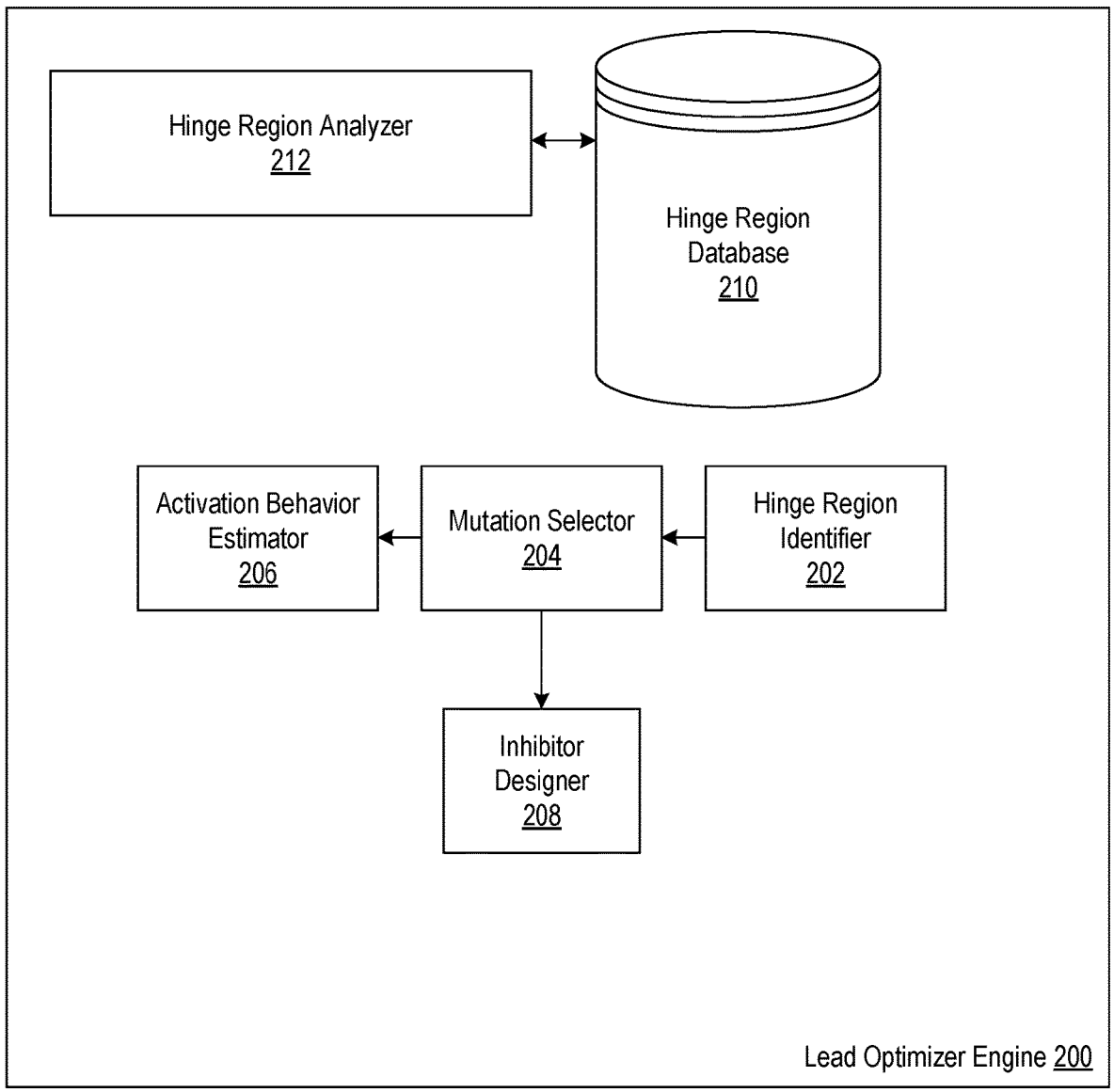
FIG. 2 is a block diagram illustrating a lead optimizer engine, in accordance with various embodiments.

FIG. 2 is a block diagram illustrating a lead optimizer engine 200, in accordance with various embodiments. The lead optimizer engine 200 can be the lead optimizer engine 124 of FIG. 1. The lead optimizer engine 200 can include a hinge region identifier module 202, a mutation selector module 204, an activation behavior estimator module 206, an inhibitor designer module 208, or any combination thereof. The lead optimizer engine 200 can maintain a hinge region database 210 (e.g., the hinge region database 126). In some embodiments, the hinge region database 210 is maintained outside of the lead optimizer engine 200, such as illustrated in FIG. 1.

The lead optimizer engine 200 can receive an identifier of a lead candidate compound. Utilizing the identifier, the hinge region identifier module 202 can access a functional compound database (e.g., the functional compound database 112A) to determine a three-dimensional structure of the lead candidate compound. Based on the three-dimensional structure, the hinge region identifier module 202 can characterize a hinge region of the lead candidate compound. The mutation selector module 204 can select a mutation that can be introduced to the hinge region based on the characterization of the hinge region according to the hinge region database 210. The mutation selector module 204 can select the mutation that is characterized in the hinge region database 210 as being able to activate functional compounds having the structural features of the identified hinge region. The mutation selector module 204 can also select a mutation introduction process corresponding to the selected mutation.

The hinge region database 210 identifies organic structures, which may be characterized as a hinge region, in various functional compounds. For example, these organic structures can be protein structures that connect to one or more domains of the functional compounds.

For example, a hinge region analyzer module 212 can generate and/or maintain the hinge region database 210 by receiving three-dimensional models (e.g., the three-dimensional structural models 104) from a data source and geometrically and/or structurally analyzing the three-dimensional models to identify the organic structures. Once the organic structure of each hinge region is identified, it is stored in the hinge region database 210 associated with the one or more domains that are capable of being connected to each hinge region. The hinge region may also be for connecting a domain to a functional region of a functional compound. Such functional region may be associated with a hinge region in the hinge region database 210.

One or more characteristics of the hinge regions may be maintained in the hinge region database. Stability and/or flexibility of a hinge region may be maintained in the hinge region database, including an efficacy rate of a functional compound associated with the flexibility factor of the hinge region. For example, a size of an amino acid structure of each hinge region may be maintained in the hinge region database. When one of the domains coupled to the hinge region includes a functional region, the size of the amino acid structure of a hinge region can indicate how much the hinge region is flexed to increase the likelihood of activation.

An operator (e.g., a computer system) of the hinge region database can input test data indicative of an activation behavior associated with the hinge regions in the hinge region database. The activation behavior estimator module 206 can then estimate the activation behavior of the hinge regions according to the test data. The activation behavior, such as efficacy of binding behavior in an animal body, is then maintained in the hinge region database. The hinge region database may be indexed to facilitate biomedical treatment configuration including designing a specific hinge region for an active molecule.

In some embodiments, the inhibitor designer module 208 is configured to identify one or more free peptides that can bind to the functional compound at or adjacent to the hinge region. When a mutation is introduced at the hinge region, the hinge region may be unstable. Introduction of a free peptide may be able to re-stabilize the hinge region. In some cases, the introduction of the free peptide can also inhibit/deactivate a functional compound having the hinge region. Accordingly, the lead optimizer engine 200 can utilize the inhibitor designer module 208 to recommend to an operator of the treatment design interface 122 a free peptide that is adapted to bind to the hinge region to counteract the effects of the mutation introduced.

In several embodiments, the inhibitor designer module 208 enables the treatment design interface 122 to provide to a treatment designer a way of both activating and deactivating a functional compound. In this manner during a biomedical treatment, a biomedical professional can introduce a specific mutation to functional compounds to activate the functional compounds and provide the mutated functional compounds to biological targets to modulate a biological process. When the treatment session is over, the inhibitor molecules (e.g., the free peptide) can then be introduced to stabilize the mutated functional compounds.

Several embodiments may include a process of utilizing the hinge region database. The process may include identifying an active group for use in a biomedical treatment session; identifying a protein domain to carry the active group; selecting, based on the protein domain, a hinge region from a hinge region database storing known characteristics of the hinge region for binding with protein domain types matching the identified protein domain; and estimating an activation behavior of a resultant compound comprising the active group and the protein domain connected to the selected hinge region. Estimating the activation behavior may be by estimating a level of activation during the biomedical treatment session based on a size of an amino acid structure in the hinge region identified in the hinge region database.

The biomedical treatment session may be a stem cell therapy session. The resultant compound may be created during the biomedical treatment session. Unlike injection therapy compounds that are pre-made, pre-purified, and/or pre-frozen, an active molecule created during the biomedical treatment session does not need to be as stable. By modifying the hinge region, the resultant compound may be slightly less stable, but would gain a significant increase in efficacy of activating active regions of the resultant compound. The resultant compound may be an enzyme, a binding protein, an antibody, or any other active organic compound with a chain structure.

Functional components (e.g., engines, modules, and databases) associated with the computer system 102 and/or the lead optimizer engine 200 can be implemented as circuitry, firmware, software, or other functional instructions. For example, the functional components can be implemented in the form of special-purpose circuitry, in the form of one or more appropriately programmed processors, a single board chip, a field programmable gate array, a network-capable computing device, a virtual machine, a cloud computing environment, or any combination thereof. For example, the functional components described can be implemented as instructions on a tangible storage memory capable of being executed by a processor or other integrated circuit chip. The tangible storage memory may be volatile or non-volatile memory. In some embodiments, the volatile memory may be considered "non-transitory" in the sense that it is not a transitory signal. Memory space and storages described in the figures can be implemented with the tangible storage memory as well, including volatile or non-volatile memory.

Each of the functional components may operate individually and independently of other functional components. Some or all of the functional components may be executed on the same host device or on separate devices. The separate devices can be coupled through one or more communication channels (e.g., wireless or wired channel) to coordinate their operations. Some or all of the functional components may be combined as one component. A single functional component may be divided into sub-components, each sub-component performing separate method step or method steps of the single component.

In some embodiments, at least some of the functional components share access to a memory space. For example, one functional component may access data accessed by or transformed by another functional component. The functional components may be considered "coupled" to one another if they share a physical connection or a virtual connection, directly or indirectly, allowing data accessed or modified by one functional component to be accessed in another functional component. In some embodiments, at least some of the functional components can be upgraded or modified remotely (e.g., by reconfiguring executable instructions that implements a portion of the functional components). The systems, engines, or devices described may include additional, fewer, or different functional components for various applications.

Figure 3:
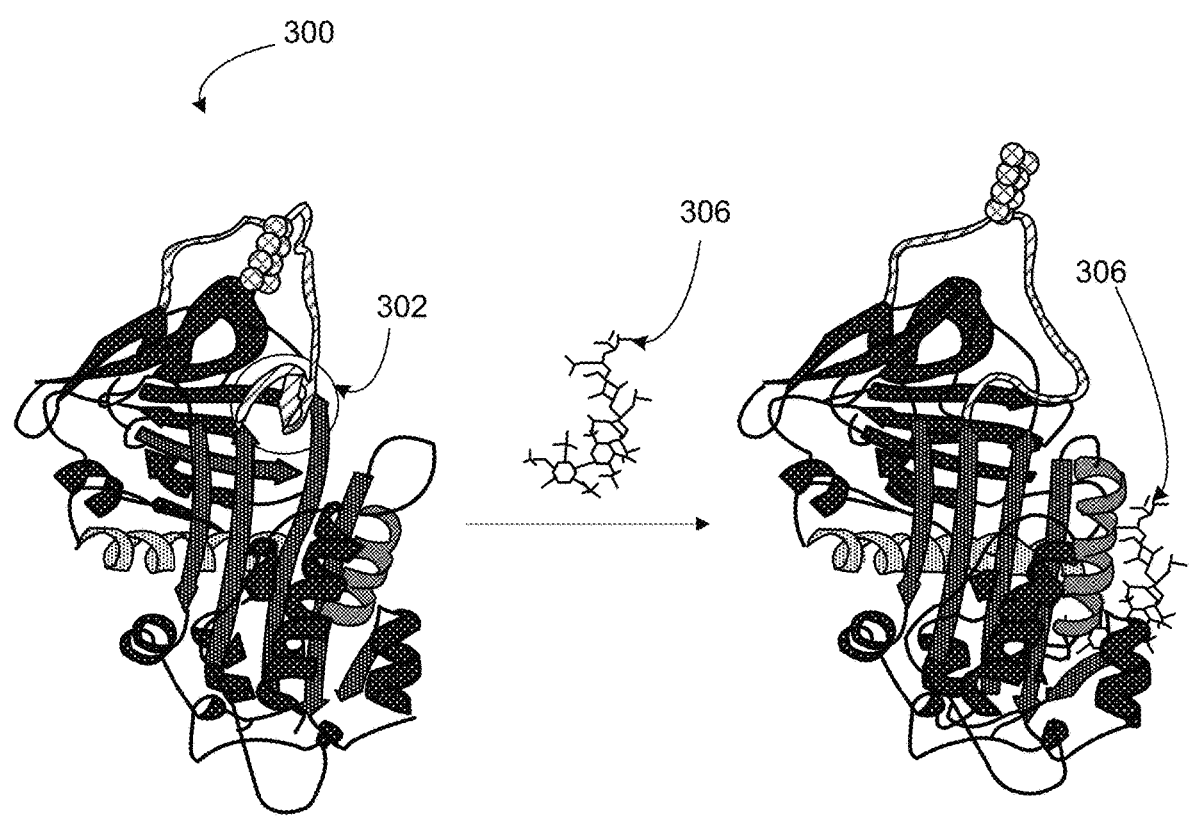
FIG. 3 is a diagram illustrating an example of a biochemical process of binding an antithrombin molecule by opening up a hinge region of the antithrombin molecule.

FIG. 3 is a diagram illustrating an example of a biochemical process of binding an antithrombin molecule 300 by opening up a hinge region 302 of the antithrombin molecule. The hinge region 302 connects two domains together. When the hinge region 302 is sufficiently "opened," the antithrombin molecule 300 can bind with a biological target 306.

Figure 4A:
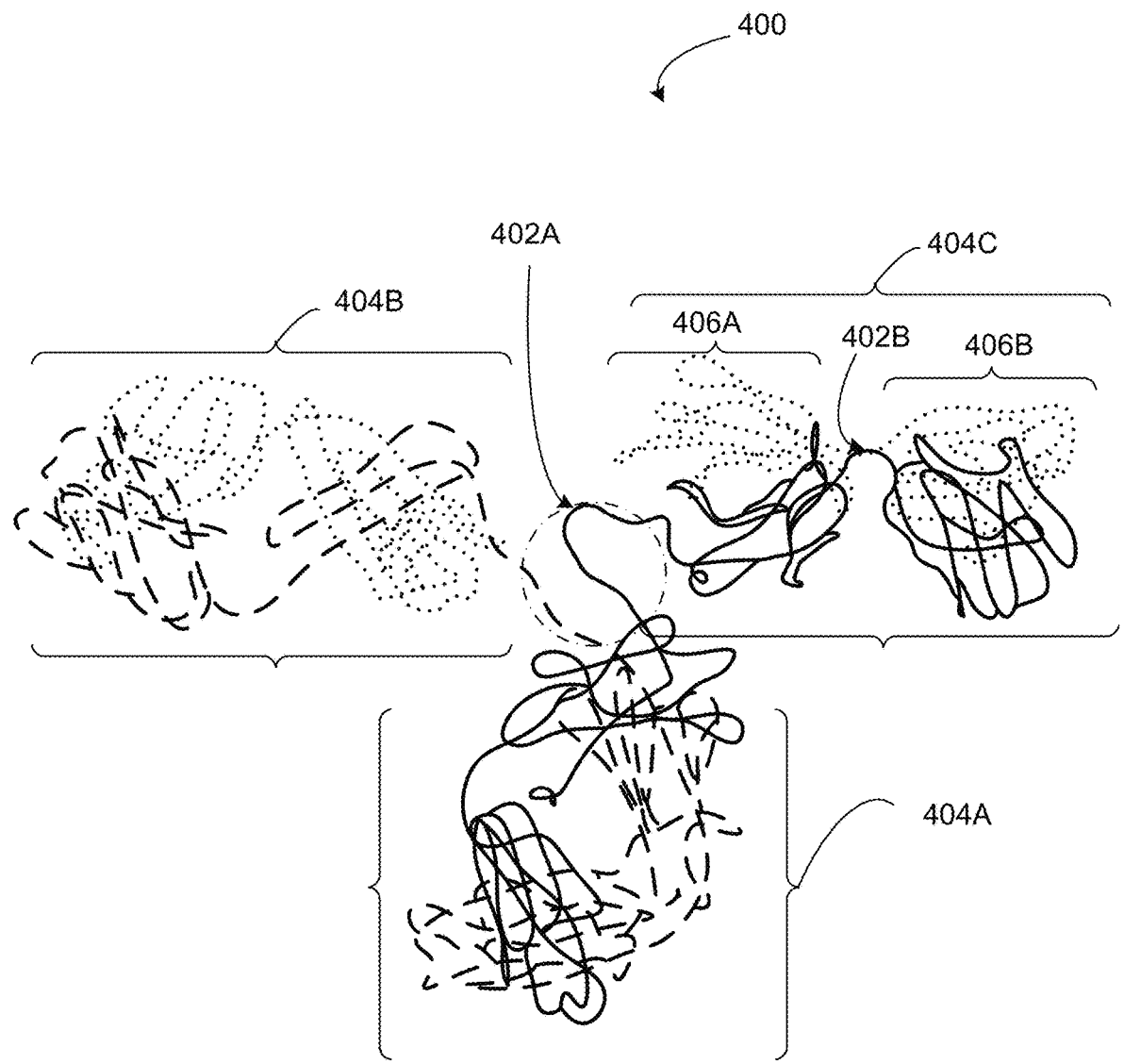
FIG. 4A is an exemplary diagram of a first antibody as a functional compound for use in a biomedical treatment.

FIG. 4A is an exemplary diagram of a first antibody as a functional compound 400 for use in a biomedical treatment. The functional compound 400 has a hinge region 402A that connects three domains (e.g., domain 404A, domain 404B, and domain 404C) together. The functional compound 400 also includes a hinge region 402B that connects two sub-domains of the domain 404C together, including a sub-domain 406A and a sub-domain 406B. For example, the sub-domain 406B can be a functional region of the functional compound 400 that can bind with a biological target.

Figure 4B:
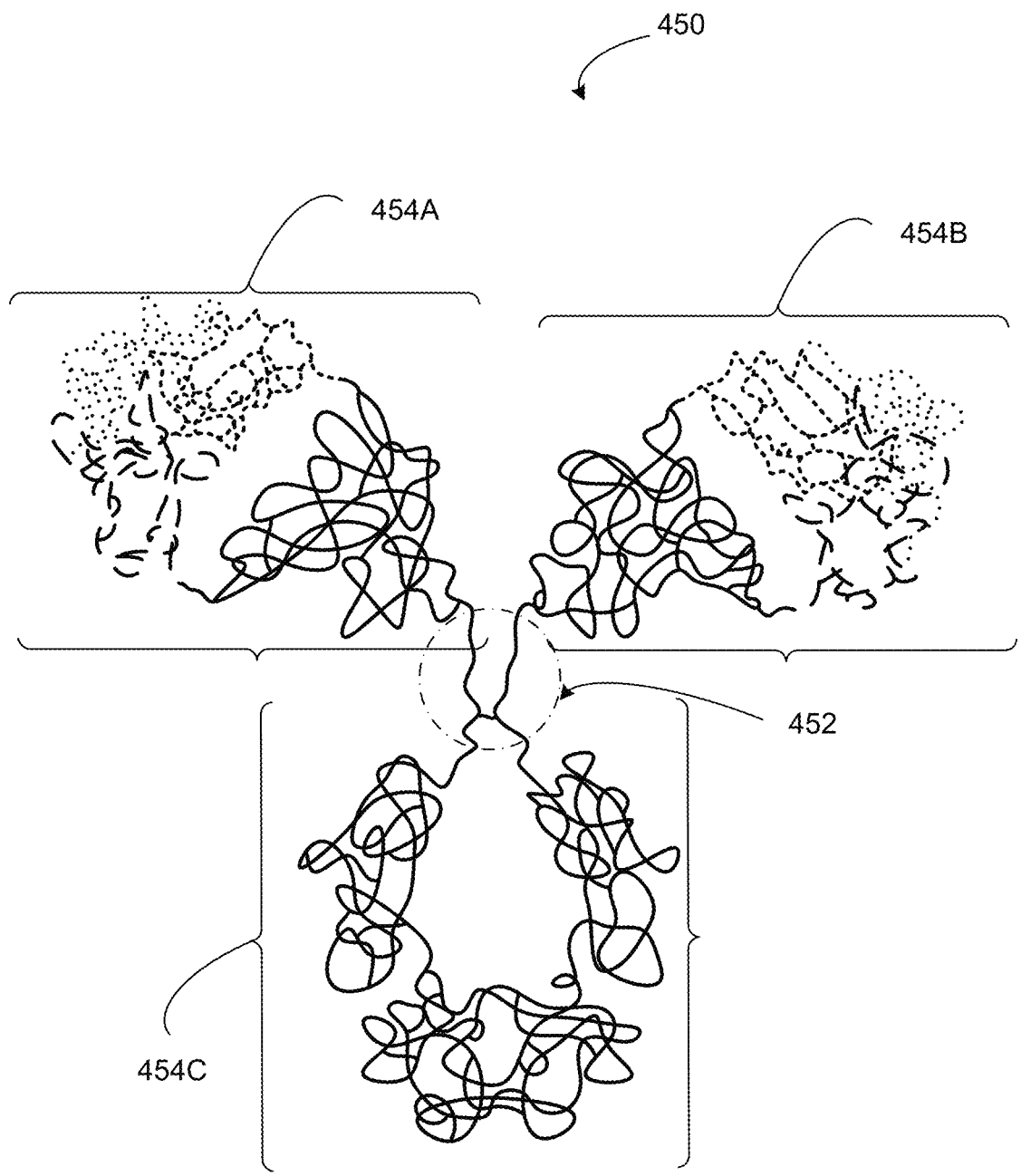
FIG. 4B is another exemplary diagram of a second antibody as a functional compound for use in a biomedical treatment.
Figure 4C:
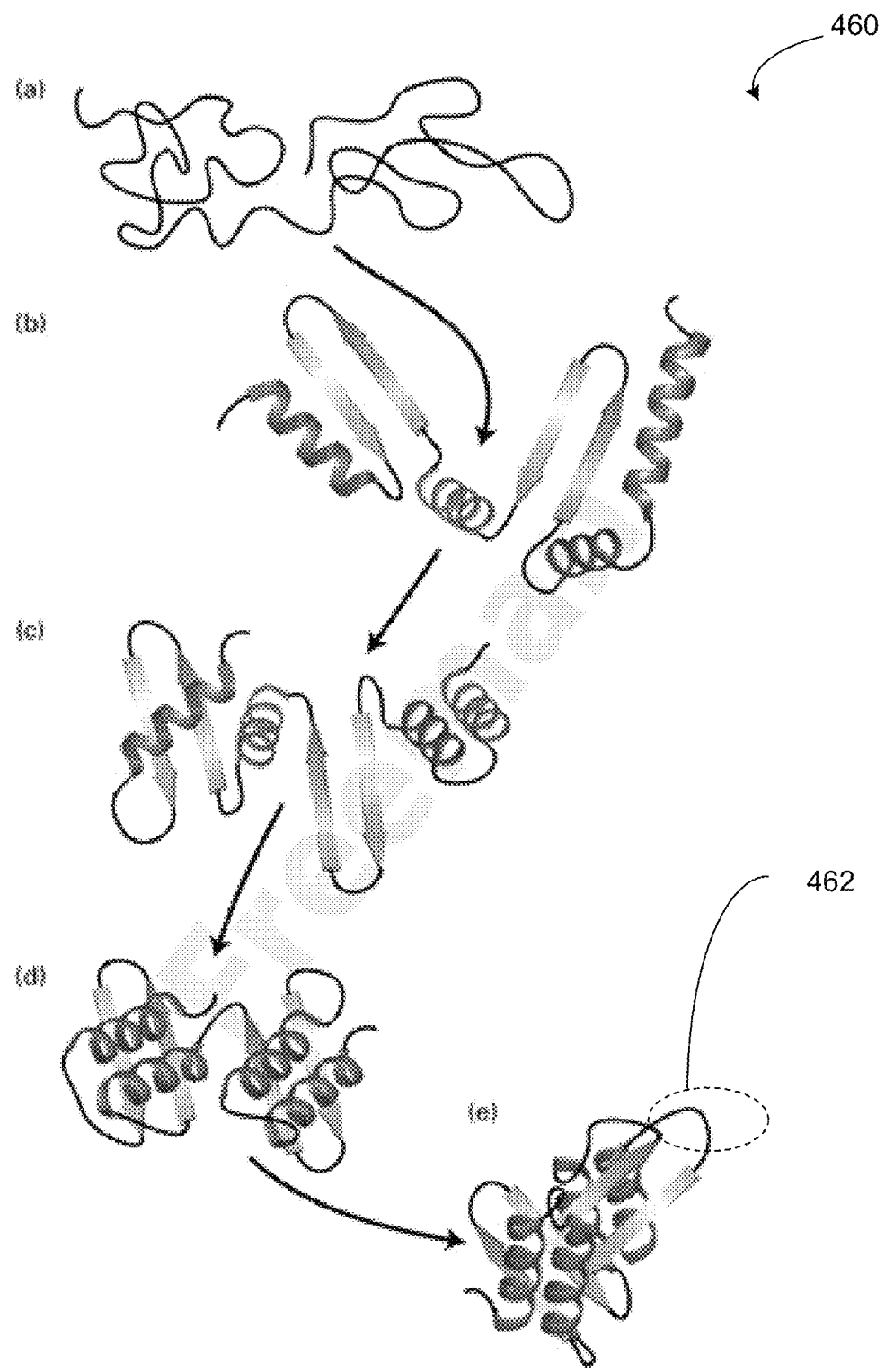
FIG. 4C is a diagram illustrating formation of a protein having a hinge region.
Figure 5:
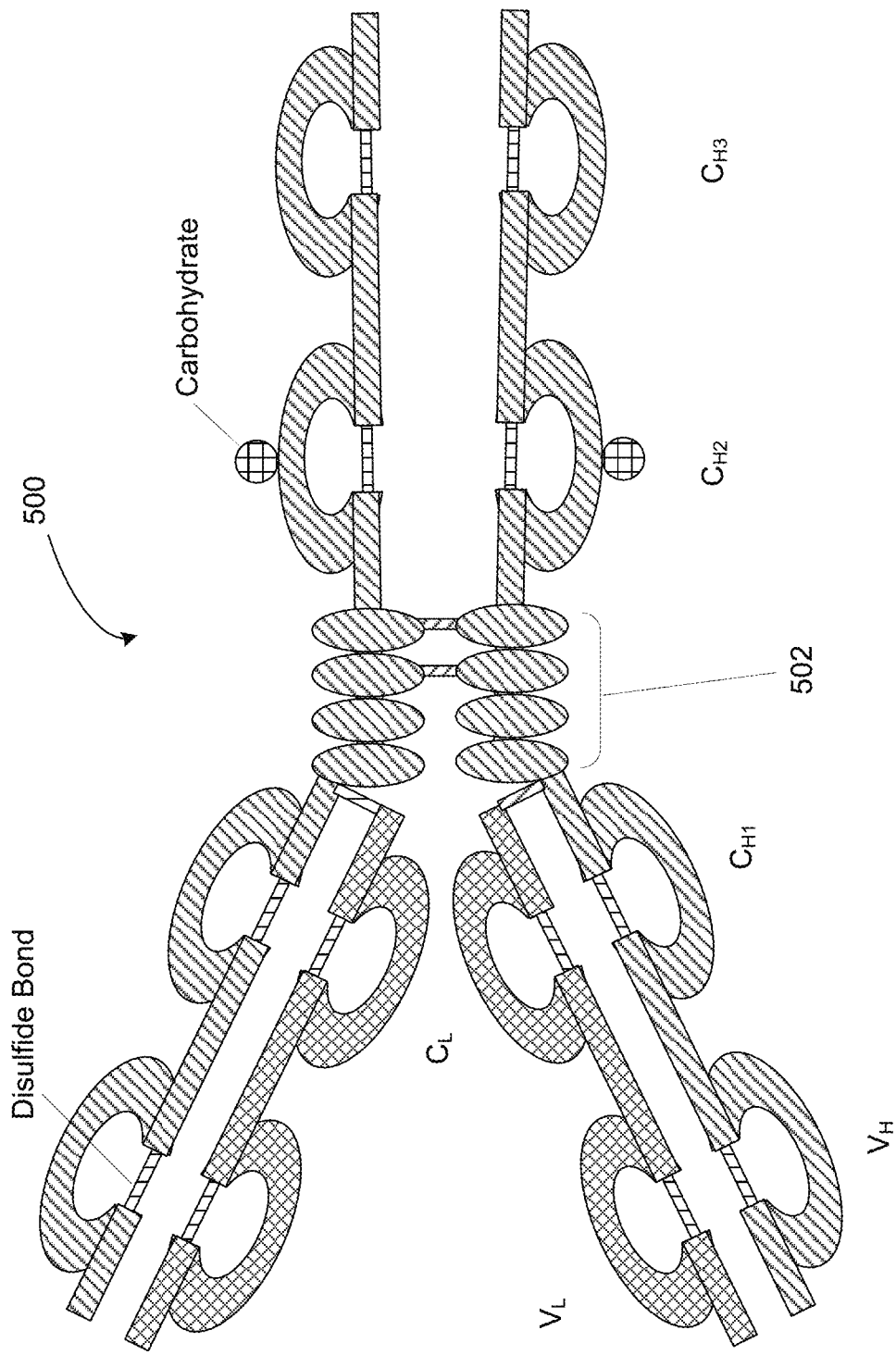
FIG. 5 is a diagram illustrating an example of a hinge region in an anti-body compound.

FIG. 4B is another exemplary diagram of a second antibody as a functional compound 450 for use in a biomedical treatment. The functional compound 450 has a hinge region 452. The hinge region 452 can connect three domains (e.g., domain 454A, domain 454B, and domain 454C). FIG. 4C is a diagram illustrating formation of a protein 460 having a hinge region 462. FIG. 5 is a diagram illustrating an example of a hinge region 502 in an antibody compound 500.

FIG. 6 is a flow chart illustrating a computer-assisted method 600 of designing a biomedical treatment, in accordance with various embodiments. At block 602, a computer system (e.g., the computer system 102 of FIG. 1 or the computer system 800 of FIG. 8) can select a compound model (e.g., in the model store 112 of FIG. 1) associated with a candidate compound that is structured to bind to a biological target to modulate the biological target into achieving a therapeutic effect. The candidate compound can be selected from a set of potential compounds identified to have a requisite characteristic corresponding to an ability to bind with the biological target. In some embodiments, the biological target is a protein structure, a cellular structure, a gene structure, a microbe feature, or any combination thereof. In some embodiments, the candidate compound is a synthetic drug or an biological molecule present in living bodies.

At block 604, the computer system can identify a structural feature in the compound model as a hinge region that connects domains in the candidate compound. At block 606, the computer system can compute a mutation process for the hinge region. For example, block 606 can include determining a mutation process to introduce a mutation at some embodiments, the test data includes a size measurement of an amino acid structure (e.g., mutable amino acid structure) in the hinge region.

At block 710, the computer system can determine an activation behavior (e.g., with and/or without the mutation) associated with the hinge region based on the test data, for example, via the activation behavior estimator module 206 of FIG. 2. For example, the computer system can determine the activation behavior by estimating a level of activation during a biomedical treatment session based on the size measurement of the amino acid structure in the hinge region.

At block 712, the computer system can associate the structural feature with the activation behavior and the compound model in a hinge region database. The computer system can also associate the mutation with the structural feature in the hinge region database. At block 714, the computer system can index the hinge region database to configure one or more biomedical treatment plans including a treatment plan to modify a specific hinge region of a candidate compound to activate the candidate compound based on the hinge region database.

While processes or methods are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. In addition, while processes or blocks are at times shown as being performed in series, these processes or blocks may instead be performed in parallel, or may be performed at different times.

Figure 8:
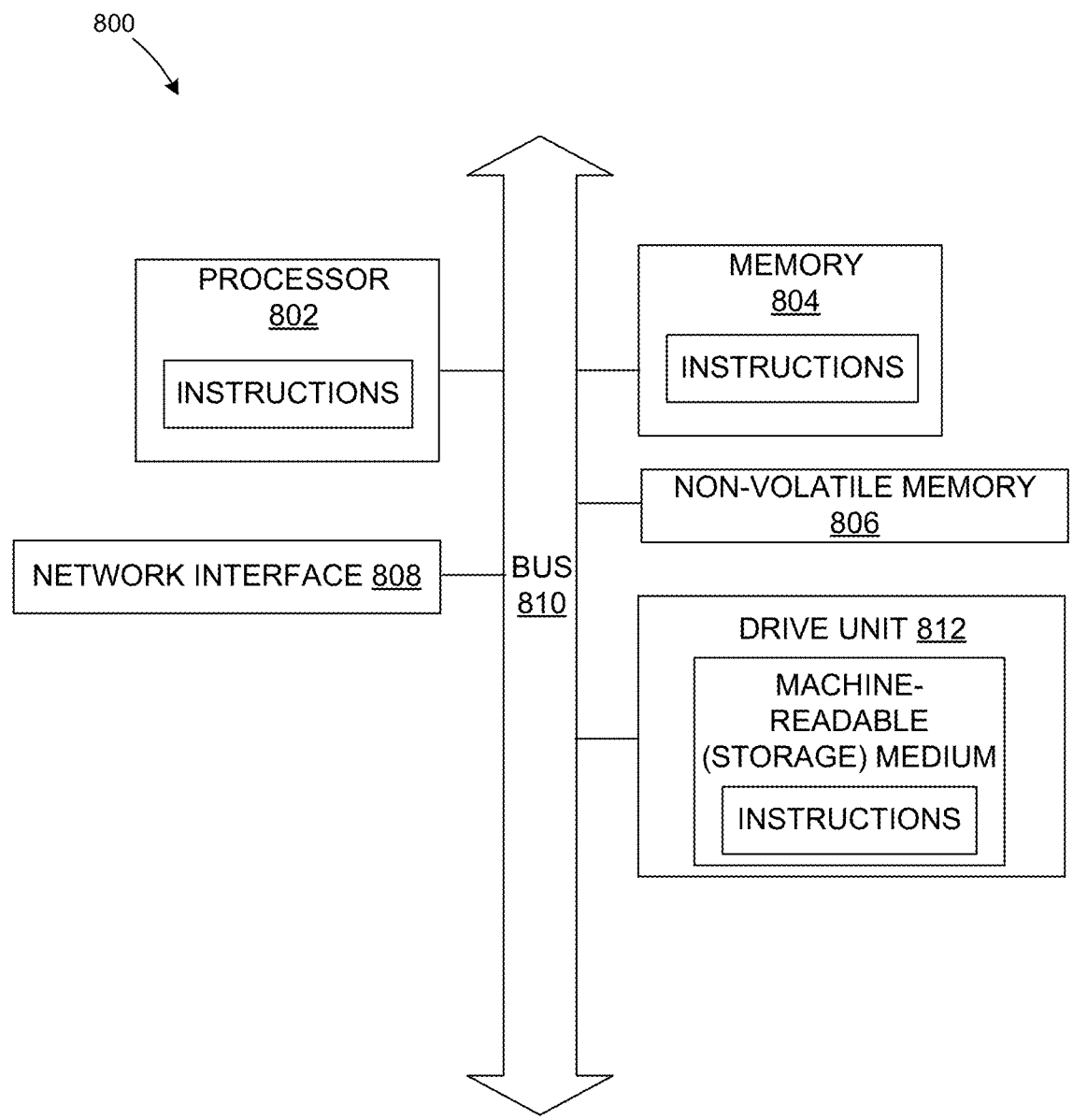
FIG. 8 is a diagrammatic representation of a machine in the example form of a computer system within which a set of instructions, for causing the machine to perform any one or more of the methodologies or modules discussed herein, may be executed.
Figures 10A, 10B, 10C:
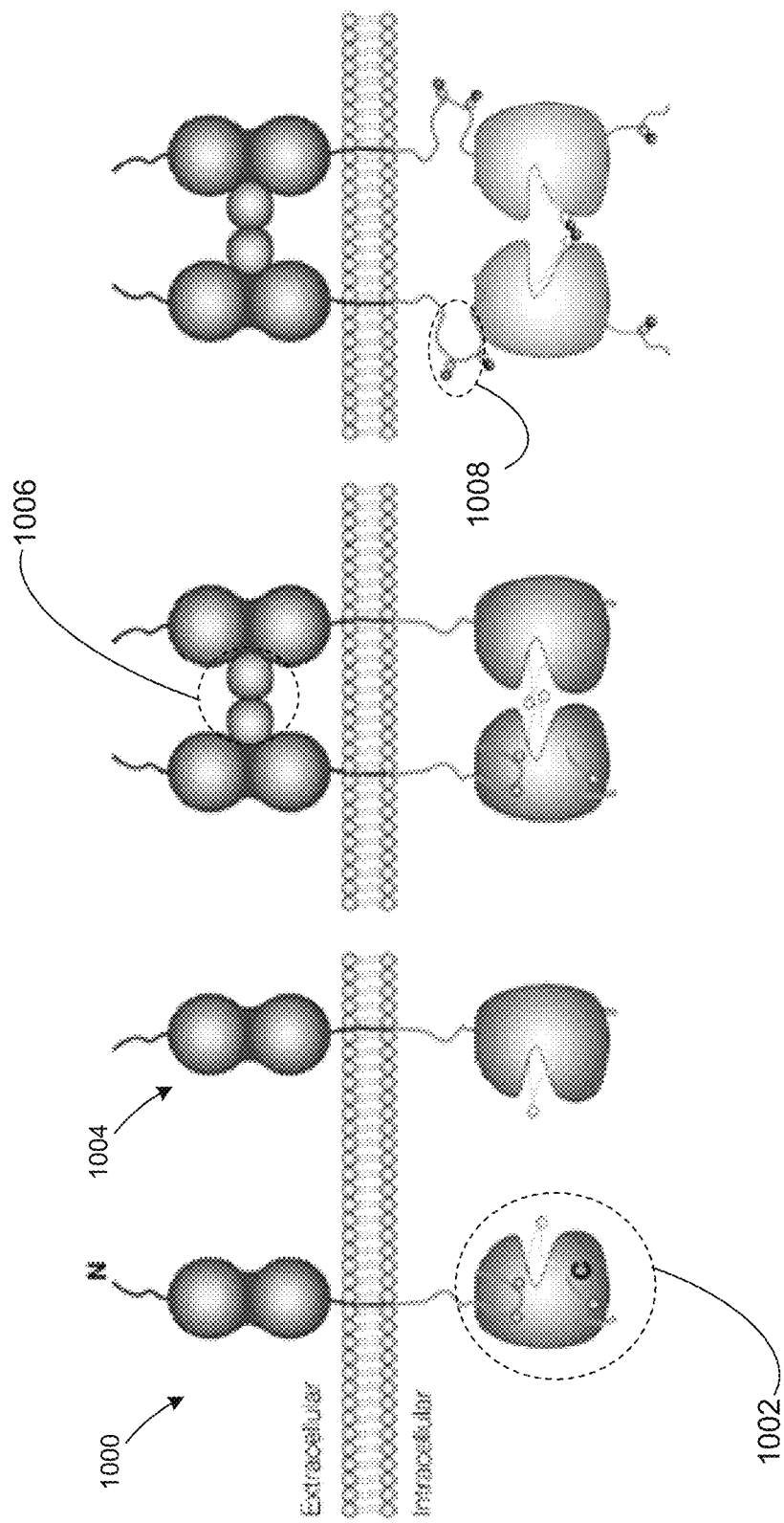
FIG. 10A is a diagram illustrating an enzyme having a functional region (i.e., an activity domain).
FIG. 10B is a diagram illustrating the enzyme binding to the biological target utilizing a ligand.
FIG. 10C is a diagram illustrating activation of the enzyme caused by the ligand.
Figure 11:
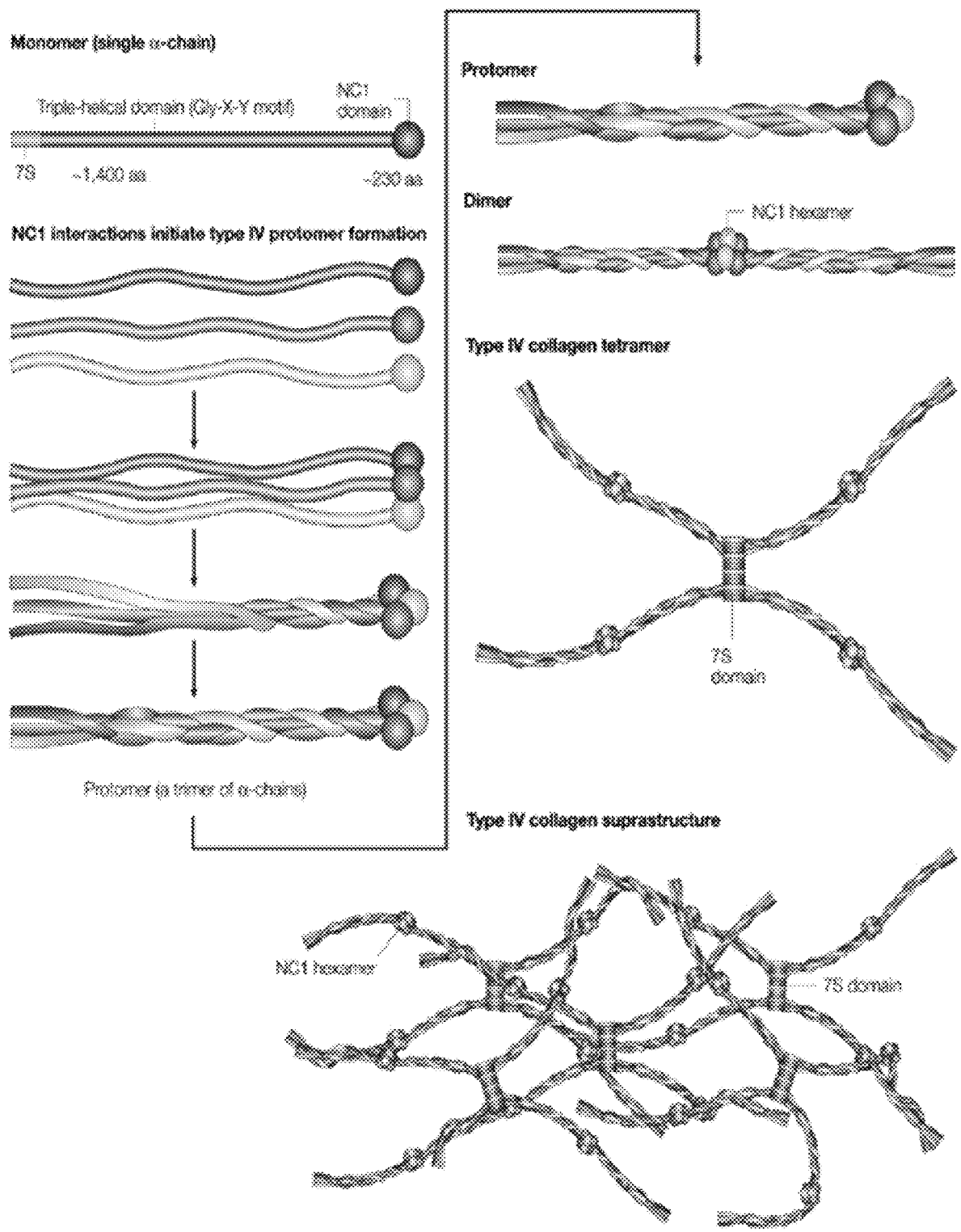
FIG. 11 is a diagram illustrating a process of assembling structural proteins.

FIG. 8 is a block schematic diagram that depicts a machine in the exemplary form of a computer system 800 within which a set of instructions for causing the machine to perform any of the herein disclosed methodologies may be executed. For example, the processes described for maintaining and using a hinge region database may be performed by the computer system 800.

In alternative embodiments, the machine may comprise or include a network router, a network switch, a network bridge, personal digital assistant (PDA), a cellular telephone, a Web appliance or any machine capable of executing or transmitting a sequence of instructions that specify actions to be taken. The computer system 800 is intended to illustrate a hardware device on which any of the instructions, processes and any other techniques, engines, modules and/or components described in this specification can be implemented. As shown, the computer system 800 includes a processor 802, memory 804, non-volatile memory 806, and a network interface 808. Various common components (e.g., cache memory) are omitted for illustrative simplicity. The computer system 800 can be of any applicable known or convenient type, such as a personal computer (PC), server-class computer or mobile device (e.g., smartphone, card reader, tablet computer, etc.). The components of the computer system 800 can be coupled together via a bus and/or through any other known or convenient form of interconnect.

One of ordinary skill in the relevant art will recognize that the terms "machine-readable (storage) medium" or "computer-readable (storage) medium" include any type of device that is accessible by the processor 802. The memory 804 is coupled to the processor 802 by, for example, a bus 810. The memory 804 can include, by way of example but not limitation, random access memory (RAM), such as dynamic RAM (DRAM) and static RAM (SRAM). The memory 804 can be local, remote, or distributed.

The bus 810 also couples the processor 802 to the non-volatile memory 806 and drive unit 812. The non-volatile memory 806 may be a hard disk, a magnetic-optical disk, an optical disk, a read-only memory (ROM), such as a CD-ROM, Erasable Programmable Read-Only Memory (EPROM), or Electrically Erasable Programmable Read-Only Memory (EEPROM), a magnetic or optical card, or another form of storage for large amounts of data. The non-volatile memory 806 can be local, remote, or distributed.

The hinge region database described may be stored in the non-volatile memory 806, the drive unit 812, or the memory 804. The processor 802 may execute one or more of the modules stored in the memory components.

The bus 810 also couples the processor 802 to the network interface 808. The network interface 808 can include one or more of a modem or network interface. A modem or network interface can be considered to be part of the computer system 800. The network interface 808 can include an analog modem, ISDN modem, cable modem, token ring interface, satellite transmission interface (e.g., "direct PC"), or other interfaces for coupling a computer system to other computer systems.

In operation, the computer system 800 can be controlled by operating system software that includes a file management system, such as a disk operating system. One example of operating system software with associated file management system software is the family of operating systems known as Windows® from Microsoft Corporation of Redmond, Washington, and their associated file management systems. Another example of operating system software with its associated file management system software is the Linux operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "generating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may thus be implemented using a variety of programming languages.

In alternative embodiments, the machine operates as a standalone device or may be connected (e.g., networked) to other machines. In a networked deployment, the machine may operate in the capacity of a server or a client machine in a client-server network environment, or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies or modules of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and storage of charge or a release of stored charge. Likewise, in other memory devices, a change of state may comprise a physical change or transformation in magnetic orientation or a physical change or transformation in molecular structure, such as from crystalline to amorphous or vice versa. The foregoing is not intended to be an exhaustive list of all examples in which a change in state for a binary one to a binary zero or vice-versa in a memory device may comprise a transformation, such as a physical transformation. Rather, the foregoing are intended as illustrative examples.

A storage medium typically may be non-transitory or comprise a non-transitory device. In this context, a non-transitory storage medium may include a device that is tangible, meaning that the device has a concrete physical form, although the device may change its physical state. Thus, for example, non-transitory refers to a device remaining tangible despite this change in state.

Potential Applications of Using a Hinge Region Database to Select a Mutation to Introduce into a Hinge Region FIG. 9 is a table illustrating different applications of activating functional compounds, in accordance with various embodiments. For example, determining a mutation process to introduce a mutation to a hinge region is applicable to DNA reprogramming therapy. A mutation can be added to the hinge region of a transcription factor or a kinase. The potential results include faster DNA binding and better regulation and yield of reprogrammed DNA. For another example, the mutation introduction process to a hinge region is applicable to DNA differentiation treatments. The mutation can be added to the hinge region of a MAP kinases. The potential results include faster DNA binding, better regulation, and a more predictable activation. For yet another example, the mutation introduction process to hinge region is applicable to protein therapy. The mutation can be added to the hinge region of structural proteins, such as integrin, dystrophin, or other anti-inflammatory proteins. The potential results include faster assembly time of the structural proteins, and higher therapeutic efficacy.

FIG. 10A is a diagram illustrating an enzyme 1000 having a functional region 1002 (i.e., an activity domain). The enzyme 1000, when active, can bind to a biological target 1004. FIG. 10B is a diagram illustrating the enzyme 1000 binding to the biological target 1004 utilizing a ligand 1006. FIG. 10C is a diagram illustrating activation of the enzyme 1000 caused by the ligand 1006. However, according to various embodiments, even in the absence of the ligand 1006, the functional region 1002 can be activated by introducing a mutation to a hinge region (e.g., a hinge region 1008) of the enzyme 1000 to achieve the same activated state as FIG. 10C.

FIG. 11 is a diagram illustrating a process of assembling structural proteins. In various embodiments, activation of structural proteins can be achieved by introducing a mutation to a hinge region of a structural protein. That is, activated proteins can assemble much faster than non-activated proteins. The assembly is critical in many genetic diseases such as muscular dystrophy, cystic fibrosis, and Epidermolysis Bullosa.

Structural proteins, such as collagen, laminin and dystrophine can be mutated at the hinge region, and facilitate the assembly of these molecules. In the case of collagen, the hinge region is somewhere near the NC1 domain. The mutation at the hinge region can facilitate the "assembly" and show the efficacy quickly since there are many genetic diseases associated with the structural protein. This approach can help overcome the efficacy issues of the current treatment for these diseases.

Figure 12:
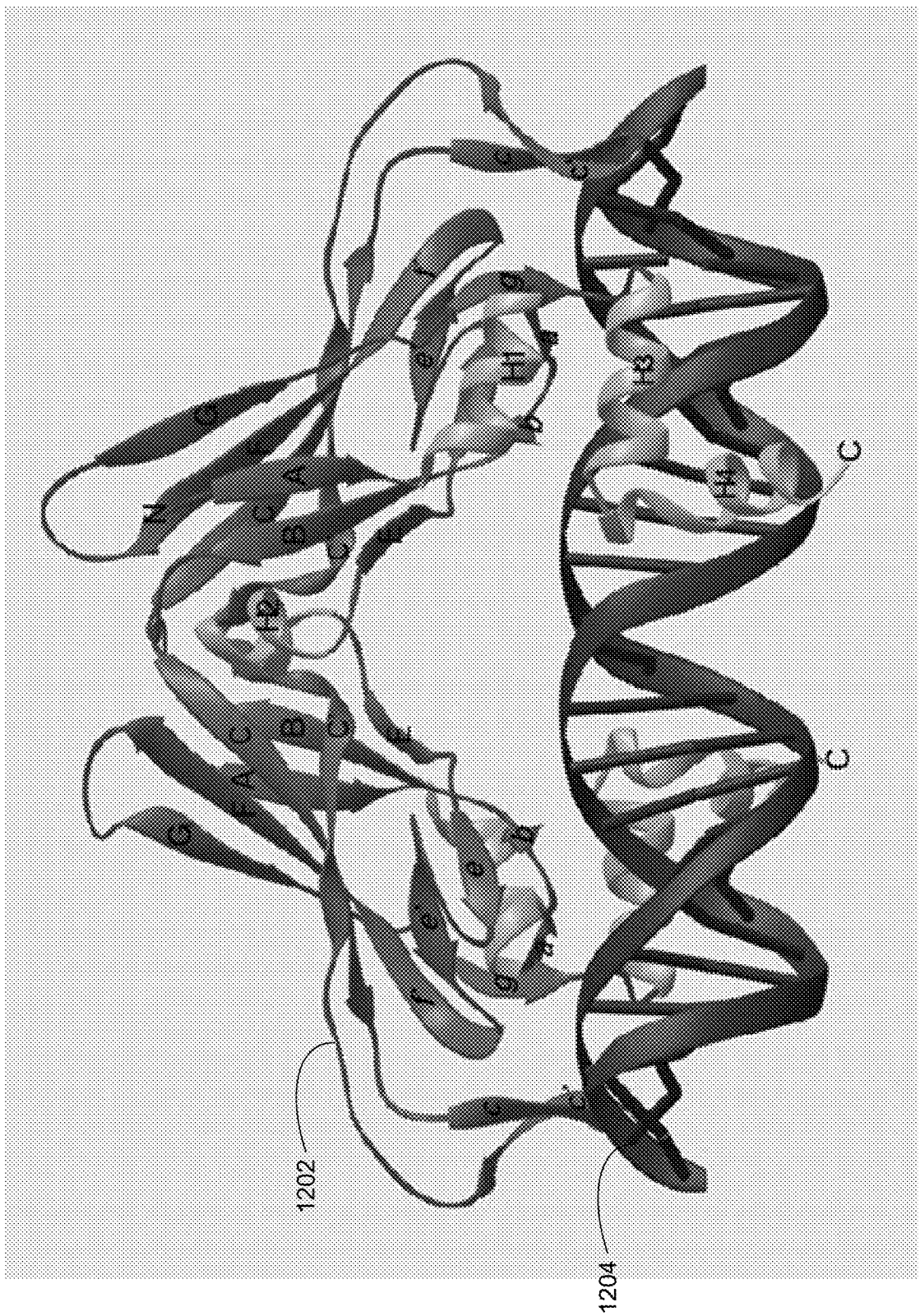
FIG. 12 is a diagram illustrating activation of a transcription factor that can be achieved by introducing a mutation to a hinge region of the transcription factor, in accordance with various embodiments.

FIG. 12 is a diagram illustrating activation of a transcription factor 1202 that can be achieved by introducing a mutation to a hinge region of the transcription factor 1202, in accordance with various embodiments. The transcription factor can be activated for faster binding to a DNA 1204.

Figure 13:
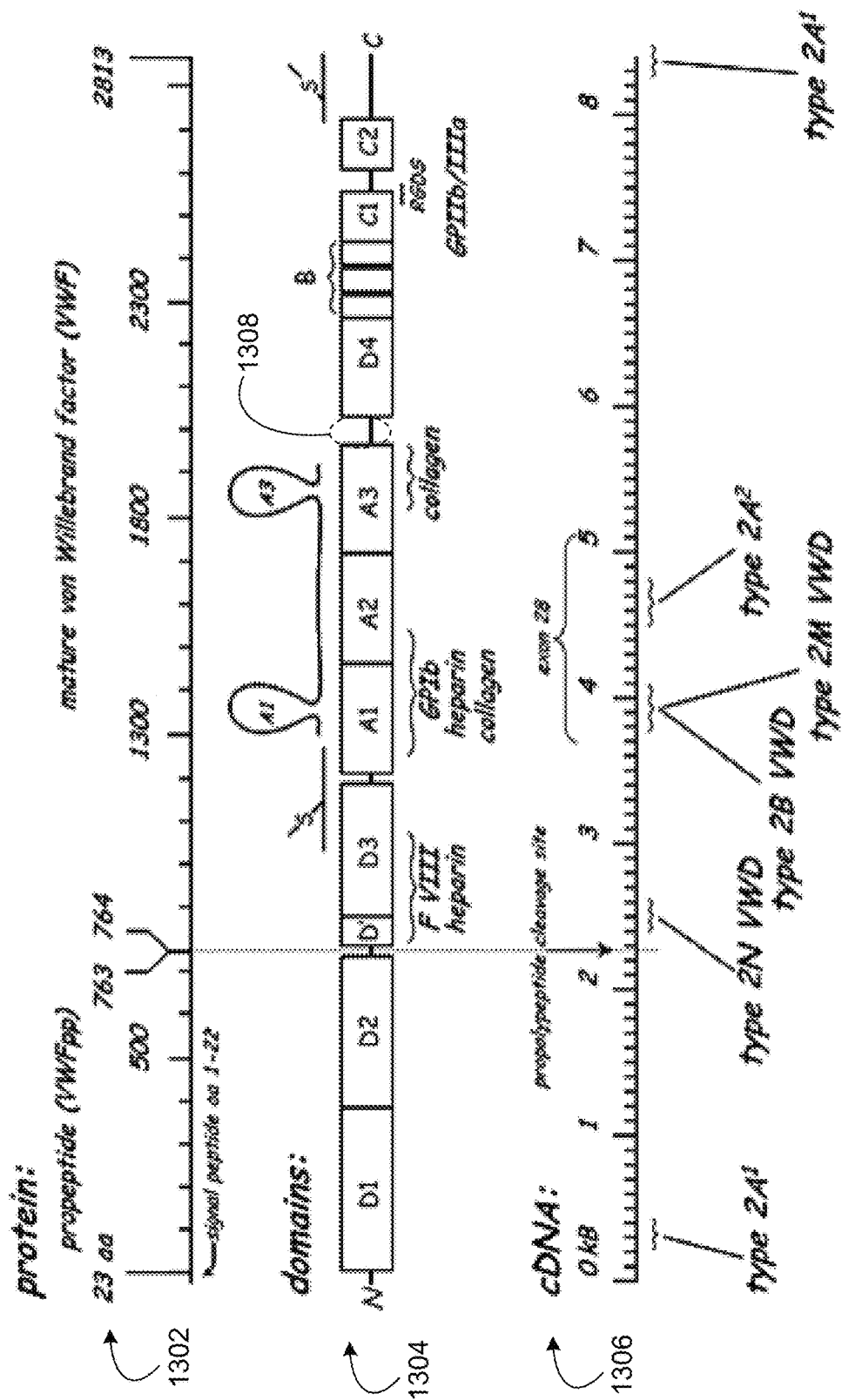
FIG. 13 is a diagram illustrating domains of a protein compound that can bind to a cDNA, in accordance with various embodiments.

FIG. 13 is a diagram illustrating domains 1304 of a protein compound 1302 that can bind to a cDNA 1306, in accordance with various embodiments.

Various embodiments include a method of introducing a mutation in a hinge region of a functional compound. For example, some embodiments can include using a computer maintaining a hinge region database to determine which mutation to introduce into which hinge region. The hinge region database can maintain associations between known structural features (e.g., protein sequence) of hinge regions and possible mutation processes and/or mutations that can fit into those structural features to "open up" the hinge regions.

For example a hinge region can be a large amino acid and the mutation can be a small amino acid (e.g., smaller than the hinge region). In the illustrated example of FIG. 13, a hinge region 1308 is between domain "A3" and domain "D4." By introducing a mutation into the hinge region 1308, the protein compound 1302 becomes activated and more easily bind to the cDNA 1306.

In various embodiments, the computer system can identify a free peptide to replace stressed hinge regions. The peptide replacements can create a new binding site for the functional compound. For example, the hinge region database can maintain associations between possible peptide replacements and the structural features (e.g., protein sequence) of the hinge regions and/or modified hinge regions (e.g., after a mutation is introduced). The computer system can generate a model for the peptide replacement. Both the modified hinge regions and the peptide replacements can provide a new rational model for future design of therapeutics treatments. Various embodiments provide computer-assisted insights into interaction of the hinge regions. For example, the peptide binding site can be a novel binding site, and provide the way to develop new drug molecules.

Cell Therapy/Gene Therapy

Expressing activated genes (e.g., with a mutation introduced to the genes' hinge regions) in cells can lead to fewer cells being required to achieve the same efficacy as compared to unmodified genes. Large amount of cells in the body requires blood supply in order to be able to survive. If the reduced amount of cells is sufficient for therapeutic use, then blood supply will not be as critical in achieve therapeutic efficacy of gene therapy.

This method can be applied to many severe genetic disorders, including immunodeficiencies, haemophilia, thalassaemia, cystic fibrosis, Epidermolysis Bullosa, Muscular Dystrophy. These diseases are caused by single gene defects. Gene therapy to treat these diseases can be more effective by using activated genes produced according to the disclosed embodiments. This method of activating genes can also facilitate more complex diseases, such as rheumatoid arthritis, e.g., by introducing activated anti-inflammatory protein expressed in stem-cell derived bone cell.

Figure 14:
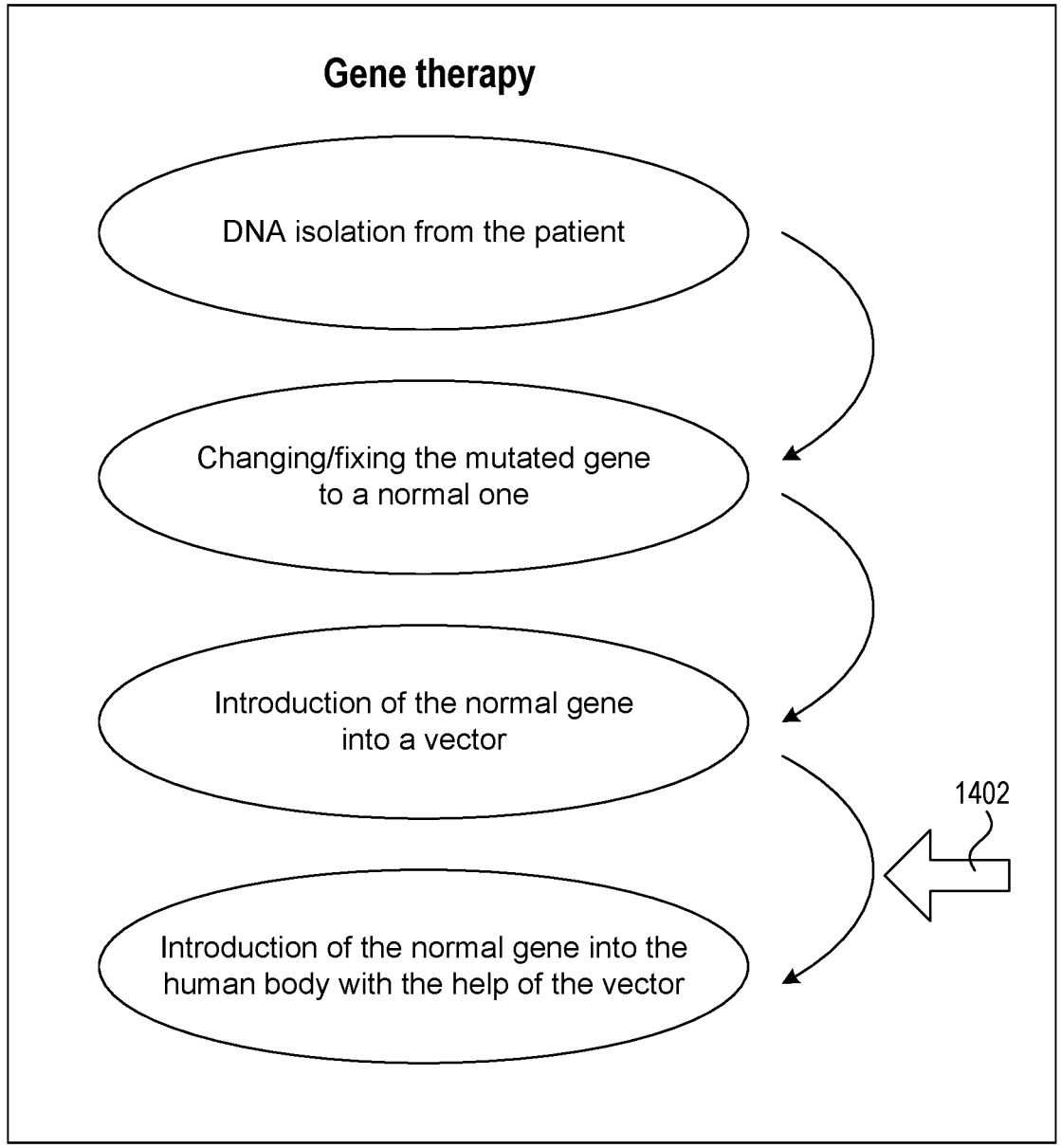
FIG. 14 is a flow chart illustrating how a conventional method of performing gene therapy can be modified in accordance with various embodiments.

FIG. 14 is a flow chart illustrating how a conventional method of performing gene therapy can be modified in accordance with various embodiments. For example, arrow 1402 illustrates how instead of introducing the "normal" gene into a vector, various embodiments include introducing an activated gene (e.g., by introducing a mutation to its hinge region) in the activated sequence.

Validation Experiment
Validated Experimental Results

Various embodiments include designing a mutation to be introduced into a hinge region of a functional compound. The improvement in activation by the introduction of the mutation in the hinge region has been validated in anti-thrombin molecules. For example, the results of the experimentation is documented in Akiko Futamura and Peter G. W. Gettins, J. Biol. Chem. 2000, 275:4092-4098. In the experimentation involving the antithrombin molecules, several point mutations, which fall in the hinge region of the antithrombin molecule, were introduced. Some of the resulting antithrombin molecules had significant activation without a co-factor (e.g., heparin). The antithrombin enzymatic activity was measured by the rate of inhibition of factor Xa by antithrombin.

There are many known mutations which are known to be responsible for tumorigenesis and the information can be found in the public database such as PDB and COSMIC. In one of the experiments, a mutation type that falls into the criteria of known "activating" mutations is selected from a published database. Test data of this mutation type served as data set A.

Independently, a 3D structural data and sequence data from a protein data bank (PDB) is loaded to a computer system. The computer system is used to virtually design and create the mutations which can activate the kinases, without looking at the mutations above. Test data of these mutations serve as data set B. When the two datasets are compared, a significant number of mutations overlapped. These results validates that the disclosed computer-assisted methodology of treatment design can potentially predict the "unknown" activating mutations. In addition, this method can automatically determine the mechanism of driver mutations found in nature. In addition, this approach can be applied to more universal activation mechanism and can be applied to other class of enzymes because of the "common" mechanism that the introduction of the mutation in the hinge region leads to more "open" conformation, and many other classes of enzyme compounds share the same structural and functional properties.

A three amino acid long peptide was also designed in the experimentation. The peptide corresponds to the hinge region of antithrombin. The peptide binds to the antithrombin based on the gel electrophoresis data.

Other Experiment Protocol

The following experiment protocol can test iPS reprogramming efficiency and reproducibility. For example, the experimental protocol includes:
1. Introducing mutations in the hinge regions of the transcription factors;
2. Using conventional vectors, such as retrovirus, adenovirus, lentivirus, or plasmid, to introduce the factors in the donor cells; and
3. Analyzing the uniformity of the iPSC generated.

The following experiment protocol can test cell therapy efficacy. For example, the experimental protocol includes:
1. Introducing a mutation (e.g., via in mutagenesis) in a protein of interest, which is defective in the diseased patient;
2. Using genome editing technology, such as TAELN and CRISPR, to introduce the sequence to the genome or artificial chromosome;
3. In the case of artificial chromosome, transferring the chromosome into the stem cell or donor's cell; and
4. In the case of bone cell expressing the anti-inflammatory protein, the cell can be introduced to Rheumatoid Arthritis animal models to test the efficacy of the cells.

In a specific example, the following is an experiment protocol to test Osteoarthritis. Osteoarthritis (OA) is degeneration of cartilage and inflammation of subchondral bone and soft tissue lining. Implantation of chondrocyte, which carries "activated" anti-inflammatory factors and differentiation factors, may lead to more effective cell therapy. NF-kB is a known anti-inflammatory protein, and BMP4 and FGF2 have been experimentally shown to increase chondrocyte differentiation. For example, the experimental protocol includes:
1. Initially, the experimental protocol can begin with an evaluation of hinge region of the proteins, such as NF-kB, BMP4 and FGF2. Use 3D structure data, sequence data, and identify the amino acid, which can be mutated to structurally "open up" these factors.
2. Conduct site-directed mutagenesis using conventional method, such as QuickChange based on Agilent Technologies™. The mutated gene is cloned into a plasmid.
3. Introduce the plasmid into the cell, preferably into the cell type which is relevant to the physiology of the disease, such as mesenchymal stem cell (MSC)-derived or iPSC-derived progenitor of chondrocytes by conventional transfection. Chondrocytes are the only cells found in cartilage.
4. These two or more proteins can be mutated and introduced to the cell together to improve the differentiation efficiency as well as the anti-inflammatory effect.
5. The resultant cells are characterized for the expression of each gene by gene expression analysis and western blotting. To evaluate the function of these proteins in cell, phosphoproteomics, such as Reverse Phase Protein Array (RPPA) (CarnaBio, Natick, MA) analysis can be employed to evaluate how the protein activation activated certain pathways. In RPPA, cells are lysed and lysates are spotted on glass slides, and each slide is probed by one phospho-specific antibody. The cell activation can be monitored by comparing cells that express wild type factors and cells that express "activated" mutated factors.
6. Transplant the cells into Collagen-Induced Arthritis (CIA) rat model.
7. Once efficacy is established, genome editing technology, such as TALEN or CRISPER combined with Human Artificial Chromosome (HAC) vector can be deployed to make more cell therapy-friendly cells. The advantage of using HAC vector is that multiple, large genes can be carried in one vector, and the vector is transferable to new host-cell background. These characteristics allow patient-specific, autologous cell transplantation.

In another specific example, the following is an experiment protocol to test epidermolysis bullosa (EB). EB is a hereditary disease that affects one in every 50,000 children. Many of the patients have mutation in collagen genes, such as collagen VII. For example, the experimental protocol includes:
1. Initially, the experimental protocol can begin with identifying a hinge region in a collagen gene, especially in the area of non-collagenous domain (NC1) and Central Triple-Helical Interrupted domain.
2. After cloning the regions, test how the regions can assemble to form trimers.

Apply appropriate modification so that the assembly can be monitored either as purified protein or in the cell. For example, the assembly in the cell can be analyzed by western blotting using the antibody specific to the assembled collagen molecules.
3. Introduce mutations and evaluate the impact on the ability to assemble.
4. Once the mutation is determined and optimized, the collagen gene construct can be introduced to Human Artificial Chromosome (HAC), which can carry a large gene sequence.
5. The vector can be introduced to the patient-derived adipose stem cell, which can be obtained by liposuction.

The following experiment protocol can test effectiveness of using a free peptide to de-stress an activated protein with a mutation in its hinge region. For example, this can be include creation of inhibitory peptide, which binds to oncogenic mutation BRAF(V600E). BRAF is a 766-amino acid, regulated signal transduction serine/threonine-specific protein kinase. The BRAF(V600E) mutation is known to be involved in some cancers, including papillary thyroid cancer and colorectal cancer. It is beneficial to obtain a peptide that binds to the novel binding region of the BRAF, since this leads to new design of therapeutics. For example, the experimental protocol includes:
1. Identify the hinge region that is determined to have "stress." For example, this can include evaluating hinge regions, such as the region 596-600.
2. Design the peptide based on the knowledge from 596-600 amino acid sequence, and other information from the hinge database. Calculate the "stress" of the region and how the peptide will replace the region.
3. Obtain or synthesize the peptide according to the design.
4. Produce the functional compound for the peptide to bind with (e.g., an activated protein). For example, The purified BRAF(V600E) protein can be obtained.
5. Characterize the binding property of the peptide by techniques, such as MicroScale Thermophoresis (NanoTemper Technologies, Munich, Germany) or other methods, such as gel electrophoresis. The inhibitory activity of the peptide can be measured by QuickScount™.
6. Determine the binding of the peptide to the protein by gel electrophoresis or by monitoring the changes in thermal stability.
7. Use the peptide to guide small molecule drug design, or convert the peptide to peptide mimetics for further development.

Advantages of Various Embodiments

More Reproducible iPS Cell Reprograming

The poor reproducibility of cell reprograming and differentiation often poses as a key bottleneck to clinical use of the iPS/stem cell therapy. iPSC generation from cells of the same person often end up with heterogeneous iPSC population. The use of activated form (e.g., via various embodiments described) of the reprograming factors (e.g., transcription factors) can improve the reproducibility of the reprograming. That is, the activation skips one step (e.g., introducing a co-factor) towards reprograming. The ratio of the improvement can depend on the environment of the transcription and how the transcription is conventionally activated.

Activation of transcription factors for iPSC reprogramming and differentiation can lead to efficient and more reproducible cell therapy production. Improved reproducibility can lead to more homogenous cell population of important cell types. Improved reproducibility can also translate into increased safety and lower cost. For example, in the case of gene therapy, more activated gene sequence can help reduce the amount of agent to show efficacy, leading to safety. Immunogenicity and blood supply issue can also be improved due to improved reproducibility.

Identification of Peptide Inhibitors

Various embodiments include a computer-assisted method of identifying peptide inhibitors to replace a stressed hinge region in a mutated functional compound. The peptide inhibitors can provide a novel binding site. The computer-assisted method can offer an alternative to antibody development that designs an antibody to bind to a target molecule. The computer system can design a peptide inhibitor to preferentially bind to a mutated (diseased) protein. This design can lead to creation of diagnostics reagents that can detect specific mutations.

This approach enables computer-assisted peptide design which binds to a functional compound (e.g., a protein structure) by replacing its hinge region. These peptides can work as an inhibitor to the functional compound. This feature is useful when both activation and deactivation are necessary for a biomedical therapy. In the case of blood clotting regulation, it is essential to control the balance of activation and inhibition.

Binding Specificity with Increased Activity

In several embodiments, a functional compound is a protein structure. Changes in an amino acid sequence of a hinge region of the functional compound generally do not affect the selectivity and specificity of the protein structure. This is advantageous because it will be easier to predict the impact of the mutation in the clinical setting, leading to safer therapeutics.

Comparison of the Hinge-Region-Based Activation Methodology to Other Types of Biomedical Treatment Design The disclosed hinge-region-based activation of functional compounds is a rational treatment design methodology. This methodology relies on a computer system's ability to identify known driver mutations as well as novel mutations that structurally matches a known hinge region. The computer system can apply various mutations to new and unknown functional compounds (e.g., protein compounds). This makes the hinge-region-based activation a cost effective design because of the high success rate.

Conventionally treatment designs may rely on a shot gun approach of designing a treatment drug or an activation agent. For the shotgun approach, while the methodology can apply to new proteins, there is a low success rate and thus is an expensive process. Other conventional approaches lack the ability to activate new and untested functional compounds (e.g., proteins).

What is claimed is:

1. A method for developing biomedical treatments designed to achieve therapeutic effects, the method comprising:

implementing, by a computer system, a virtual screening process on a first database of models, so as to identify a set of models corresponding to a set of candidate compounds determined to have a requisite characteristic corresponding to an ability to bind with a biological target,
    wherein each model in the set of models is associated with a different one of the set of candidate compounds;
evaluating, by the computer system in accordance with one or more evaluation processes, the set of models, so as to select, from amongst the set of models, a first model of a candidate compound that is structured to modulate the biological target, wherein modulation of the biological target is hypothesized to have a therapeutic effect;
identifying, by the computer system, a structural feature of the first model of the candidate compound as a hinge region,
    wherein the hinge region represents an interconnecting region of the candidate compound that connects at least two different domains, the different domains including (i) a functional region that is able to bind to the biological target and (ii) a non-functional region that is not able to bind to the biological target;
selecting, by the computer system from a second database in which mutations are characterized, a mutation that, when introduced to the hinge region, results in the functional region being distanced from the non-functional region, such that the functional region is more accessible for binding purposes;
generating, by the computer system, an updated first model of a mutated candidate compound that includes the mutation at the hinge region;
storing, by the computer system, the updated first model in a database;
identifying, by the computer system, a second model of a free peptide molecule structured to bind to the mutated candidate compound at the hinge region,
    wherein introduction of the free peptide molecule at the hinge region inhibits the effect of the mutation;
presenting, by the computer system, the updated first model and the second model on a treatment design interface as a candidate for a biomedical treatment;
providing, by the computer system, the updated first model and the second model to at least one synthesizer machine coupled to the treatment design interface, so as to facilitate synthesis of the mutated candidate compound and the free peptide molecule; and
administering the mutated candidate compound to living cells and subsequently administering the free peptide molecule to the living cells.

2. The method of claim 1, further comprising:
determining, by the computer system, synthesis processes for creating the mutated candidate compound and the free peptide molecule.

3. The method of claim 2, wherein the living cells are included in a living body to which the mutated candidate compound and the free peptide molecule are administered to achieve a desired therapeutic effect.

4. The method of claim 1, further comprising:
designing, by the computer system, a mutation process to occur during the biomedical treatment,
    wherein upon the mutation process being completed, a functional compound is produced in accordance with the updated first model without pre-making, pre-purifying, or pre-freezing the functional compound before the biomedical treatment.

5. The method of claim 4, wherein the functional compound is an enzyme for a cell therapy.

6. The method of claim 4, wherein the functional compound is a binding protein for a gene activation therapy.

7. The method of claim 1, wherein the biological target is a protein structure, a cellular structure, a gene structure, a microbe feature, or any combination thereof.

8. The method of claim 1, wherein the candidate compound represented by the first model is a synthetic drug.

9. The method of claim 1, wherein the candidate compound represented by the first model is a biological molecule naturally present in living human bodies.

10. The method of claim 1, further comprising:
receiving, by the computer system,
  (i) the set of models,
  (ii) three-dimensional images of the set of candidate compounds,
  (iii) ligand data that identifies ligands that are able to bind to the biological target and/or the set of candidate compounds, and
  (iv) synthesis data that specifies processes for biochemically synthesizing the set of candidate compounds; and
aggregating, by the computer system, (i) the set of models, (ii) the three-dimensional images, (iii) the ligand data, and (iv) the synthesis data into a datastore, such that each model in the set of models is associated with at least one of the three-dimensional images, at least some of the ligand data, and at least some of the synthesis data.

11. The method of claim 1, wherein the virtual screening process is a computational technique that automatically evaluates each model in the set of models against a receptor area of the biological target to identify structures of the set of candidate compounds most likely to bind with the biological target.

12. The method of claim 11, wherein the virtual screening process includes identifying ligands that are able to bind to the receptor area of the biological target and then determining similarity between the ligands and each model in the set of models.

13. The method of claim 12, further comprising:
outputting, by the computer system, a list of the set of candidate compounds based on an outcome of the virtual screening process.

14. The method of claim 13, wherein the candidate compound represented by the first model is selected from the list based on the one or more evaluation processes.

15. The method of claim 14, wherein the one or more evaluation processes include biochemical testing, toxicity verification, dose response, orthogonal testing, secondary structural screening, synthesis feasibility evaluation, biophysical testing, or any combination thereof.

16. The method of claim 1, further comprising:
presenting, by the computer system, the second model on the treatment design interface as an option for stabilization following the biomedical treatment.

17. The method of claim 1, further comprising:
determining, by the computer system, a first synthesis process for creating the mutated candidate compound;
determining, by the computer system, a second synthesis process for creating the free peptide molecule; and
presenting, by the computer system, the first and second synthesis processes on the treatment design interface through which a user is able to initiate or facilitate synthesis of the mutated candidate compound and the free peptide molecule.

18. A computer-implemented method for developing biomedical treatments designed to achieve therapeutic effects, the method comprising:
implementing, by the computer system, a virtual screening process on a first database of models, so as to identify a set of models corresponding to a set of candidate compounds determined to have a requisite characteristic corresponding to an ability to bind with a biological target,
  wherein each model in the set of models is associated with a different one of the set of candidate compounds;
evaluating, by the computer system in accordance with one or more evaluation processes, the set of models, so as to select, from amongst the set of models, a first model of a candidate compound that is structured to modulate the biological target, wherein modulation of the biological target is hypothesized to have a therapeutic effect,
  wherein the one or more evaluation processes include processes undertaken by the computer system and processes undertaken by human actors;
identifying, by the computer system, a structural feature of the first model as a hinge region,
  wherein the hinge region represents an interconnecting region of the candidate compound that connects at least two different domains, the different domains including (i) a functional region that is able to bind to the biological target and (ii) a non-functional region that is not able to bind to the biological target;
selecting by the computer system from a second database in which mutations are characterized, a mutation that, when introduced to the hinge region, results in the functional region being distanced from the non-functional region, such that the functional region is more accessible for binding purposes;
generating, by the computer system, an updated first model of a mutated candidate compound that includes the mutation at the hinge region;
storing, by the computer system, the updated first model in a database;
identifying, by the computer system, a second model of a free peptide molecule structured to bind to the mutated candidate compound at the hinge region,
 wherein introduction of the free peptide molecule at the hinge region inhibits the effect of the mutation;

determining, by the computer system, synthesis processes for creating the mutated candidate compound and the free peptide molecule;

presenting, by the computer system, the updated first model, the second model, and the corresponding synthesis processes on a treatment design interface as a candidate for a biomedical treatment; and providing, by the computer system to at least one synthesizer machine coupled to the treatment design interface, the updated first model to facilitate synthesis of the mutated candidate compound and the second model to facilitate synthesis of the free peptide molecule; and administering the mutated candidate compound to a living body and subsequently administering the free peptide molecule into the living body, such that the mutated candidate compound modulates a biological process to effect the biomedical treatment and the free peptide molecule stabilizes the mutated candidate compound to inhibit modulation of the biological process.

19. A method comprising:
developing, by a computer system, a biomedical treatment by—
  screening a first database of models to identify a set of models corresponding to a set of candidate compounds that are determined to have a requisite characteristic corresponding to an ability to bind with a biological target, wherein each model in the set of models is associated with a different one of the set of candidate compounds;
  evaluating the set of models to select, from amongst the set of models, a first model of a candidate compound that is structured to modulate the biological target, wherein modulation of the biological target is hypothesized to have a therapeutic effect;
  identifying a structural feature of the first model as representative of a hinge region, wherein the hinge region represents an interconnecting region of the candidate compound that connects at least two different domains, the different domains including (i) a functional region that is able to bind to the biological target and (ii) a non-functional region that is not able to bind to the biological target;
  selecting, from a second database in which mutations are characterized, a mutation that, when introduced to the hinge region, results in the functional region being distanced from the non-functional region, such that the functional region is more accessible for binding purposes;
  generating an updated first model of a mutated candidate compound that is representative of the candidate compound with the mutation at the hinge region;
  identifying a free peptide molecule that is able to bind to the mutated candidate compound at the hinge region, thereby inhibiting the effect of the mutation;
  determining processes for synthesizing the mutated candidate compound and the free peptide molecule; and
  providing, to at least one synthesizer machine, information regarding the processes to facilitate synthesis of the mutated candidate compound and the free peptide molecule; and
introducing the mutated candidate compound to living cells and subsequently administering the free peptide molecule to the living cells.

20. The method of claim 19, wherein the living cells are included in a living body to which the mutated candidate compound and the free peptide molecule are administered to achieve a desired therapeutic effect.

21. The method of claim 19, wherein the living cells are included in a cell culture.

22. The method of claim 19, wherein the biological target is a specific type of cell, a specific region of deoxyribonucleic acid, a specific protein, or any combination thereof.

23. The method of claim 19, wherein the living cells are stem cells to be introduced into a living body to achieve a desired therapeutic effect.

* * * * *